(12) United States Patent
Zhang et al.

(10) Patent No.: US 11,154,664 B2
(45) Date of Patent: Oct. 26, 2021

(54) INTERFACE OF NEEDLE OF MEDICAL SYRINGE

(71) Applicant: Shanghai Boqia Medical Device Co., Ltd., Shanghai (CN)

(72) Inventors: Yiyi Zhang, Shanghai (CN); Zuren Zhang, Shanghai (CN); Weihua Xu, Shanghai (CN)

(73) Assignee: SHANGHAI BOQIA MEDICAL DEVICE CO., LTD., Shanghai (CN)

( * ) Notice: Subject to any disclaimer, the term of this patent is extended or adjusted under 35 U.S.C. 154(b) by 161 days.

(21) Appl. No.: 16/082,169

(22) PCT Filed: Nov. 3, 2017

(86) PCT No.: PCT/CN2017/109253
§ 371 (c)(1),
(2) Date: Sep. 4, 2018

(87) PCT Pub. No.: WO2018/209899
PCT Pub. Date: Nov. 22, 2018

(65) Prior Publication Data
US 2021/0220571 A1     Jul. 22, 2021

(30) Foreign Application Priority Data

May 16, 2017 (CN) .......................... 201710345517.8
Oct. 18, 2017 (CN) .......................... 201710967791.9

(51) Int. Cl.
*A61M 5/34* (2006.01)
*A61M 5/315* (2006.01)
*A61M 5/31* (2006.01)

(52) U.S. Cl.
CPC ............ *A61M 5/34* (2013.01); *A61M 5/3129* (2013.01); *A61M 5/31511* (2013.01); *A61M 2005/3126* (2013.01)

(58) Field of Classification Search
CPC ... A61M 5/34; A61M 5/31511; A61M 5/3129
See application file for complete search history.

(56) References Cited

U.S. PATENT DOCUMENTS

2002/0010433 A1* 1/2002 Johnson ................ A61M 5/347
604/241

* cited by examiner

*Primary Examiner* — Bradley J Osinski
(74) *Attorney, Agent, or Firm* — Tianhua Gu; Global IP Services

(57) ABSTRACT

An interface of the needle of a medical syringe and realizes that a conical fitting and a conical inclined surface of a syringe barrel and a conical lip and a conical hole of the needle form an interface of the needle; when the conical hole of the needle is plugged onto the conical fitting of the syringe barrel, the needle is fixed onto the conical fitting of the syringe barrel to achieve the purpose of preventing a needle tip from swinging when the needle pierces a muscle or a blood vessel of a human body, so as to avoid misoperation; and after the medical syringe is used, the conical lip of the needle distal away from the needle tip only needs to be pinched flat, the needle can then be separated from the conical fitting of the syringe barrel of the medical syringe.

12 Claims, 16 Drawing Sheets

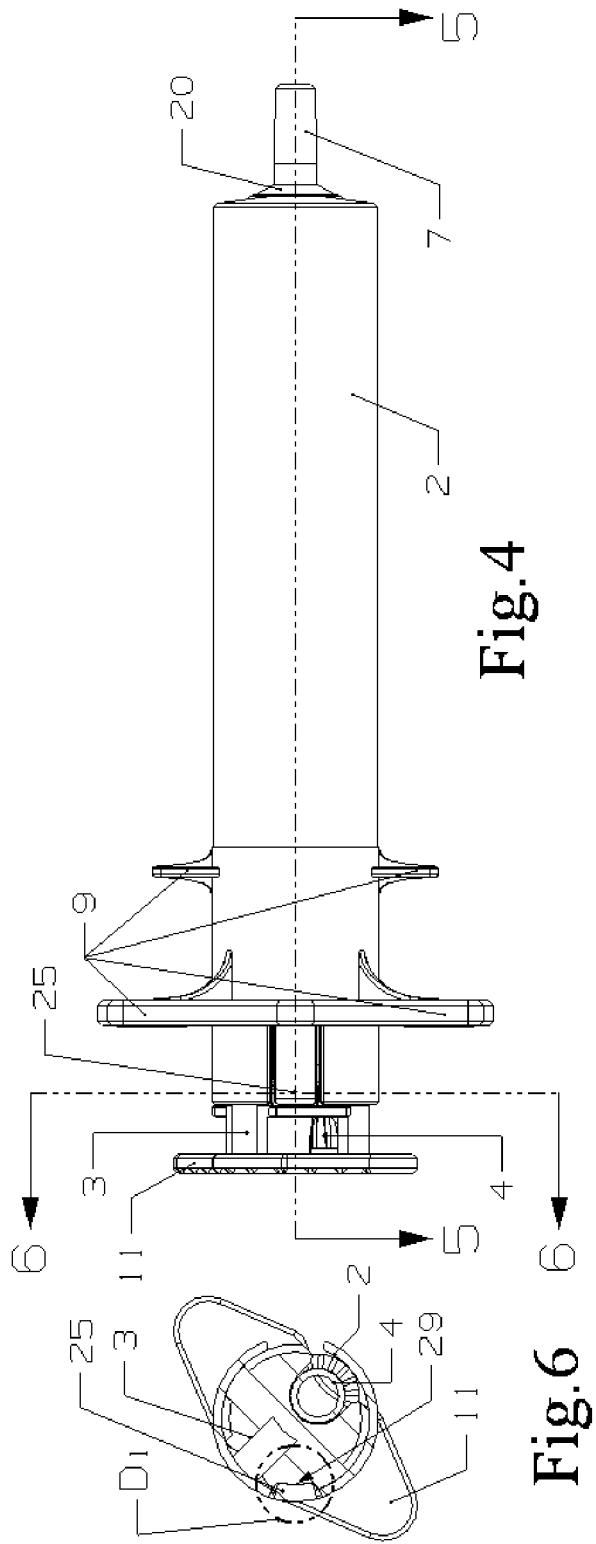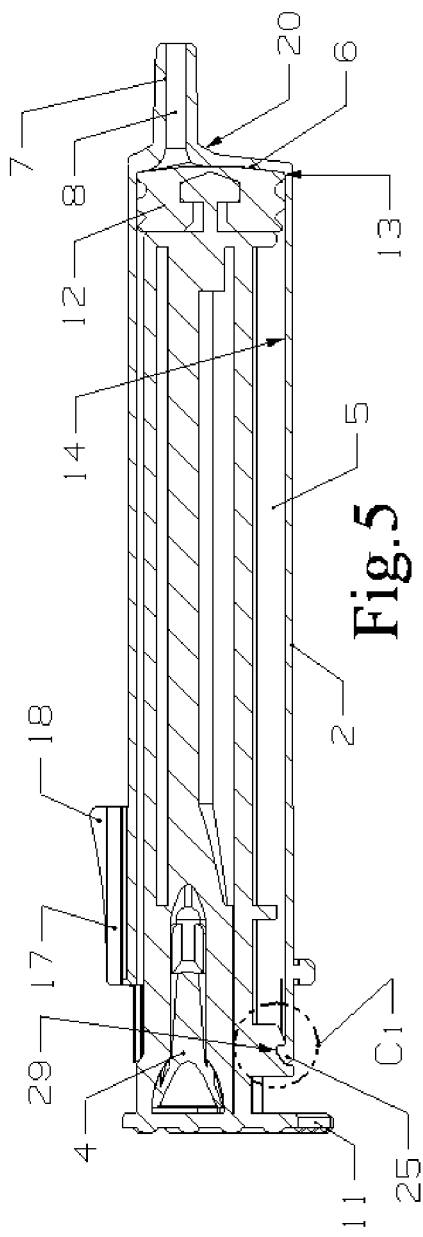

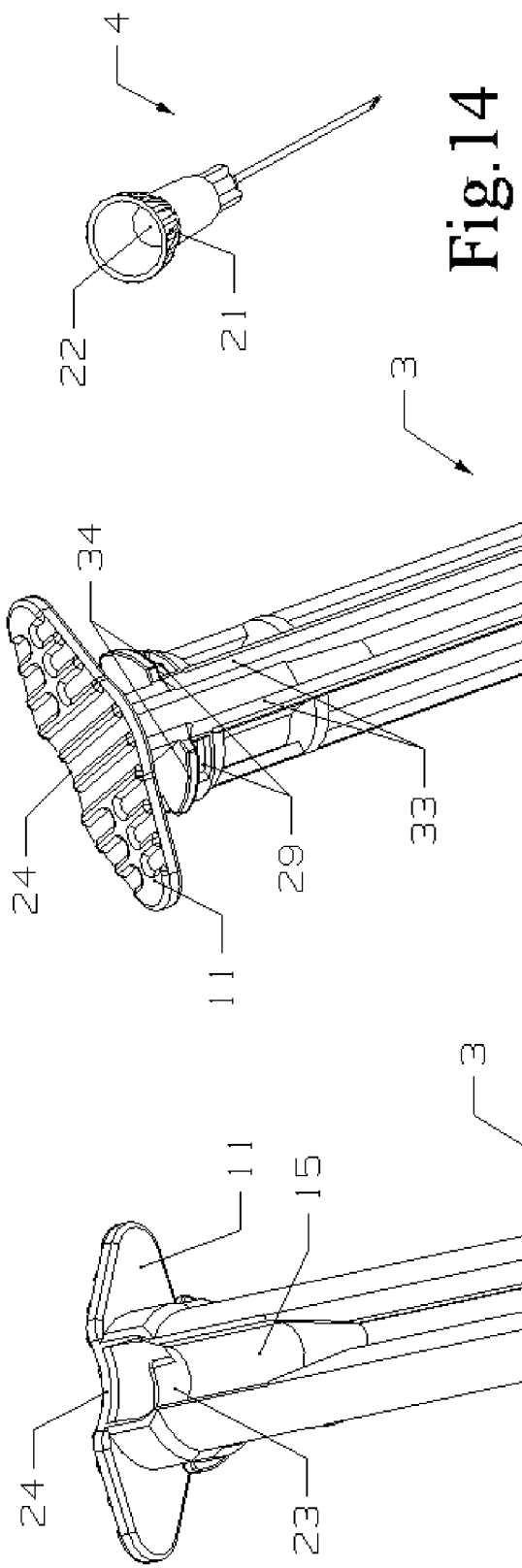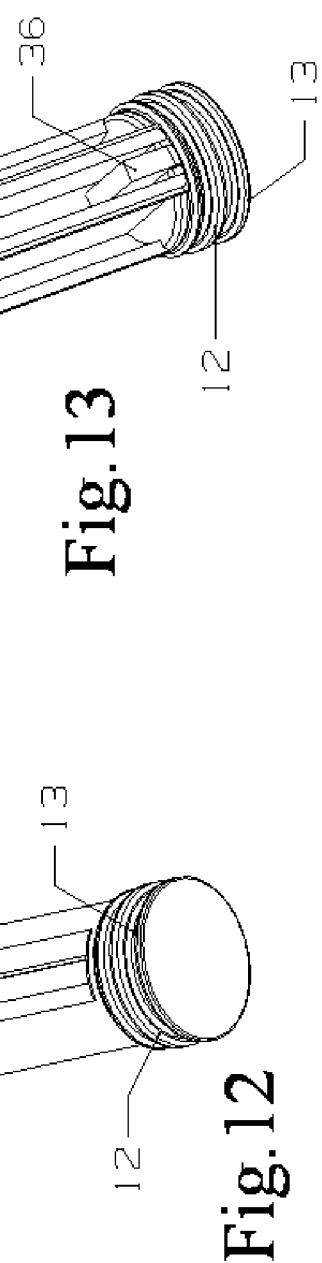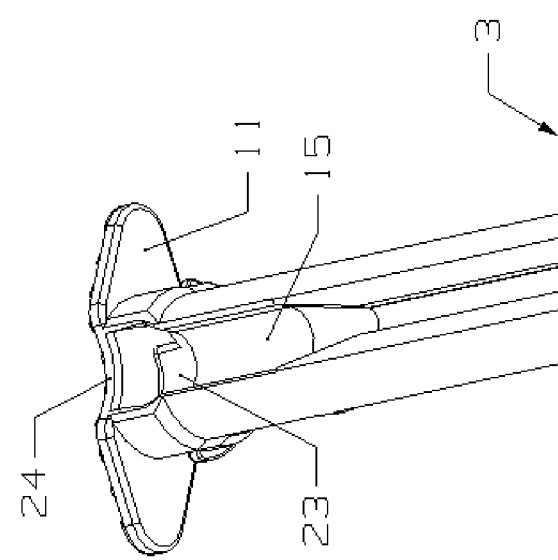

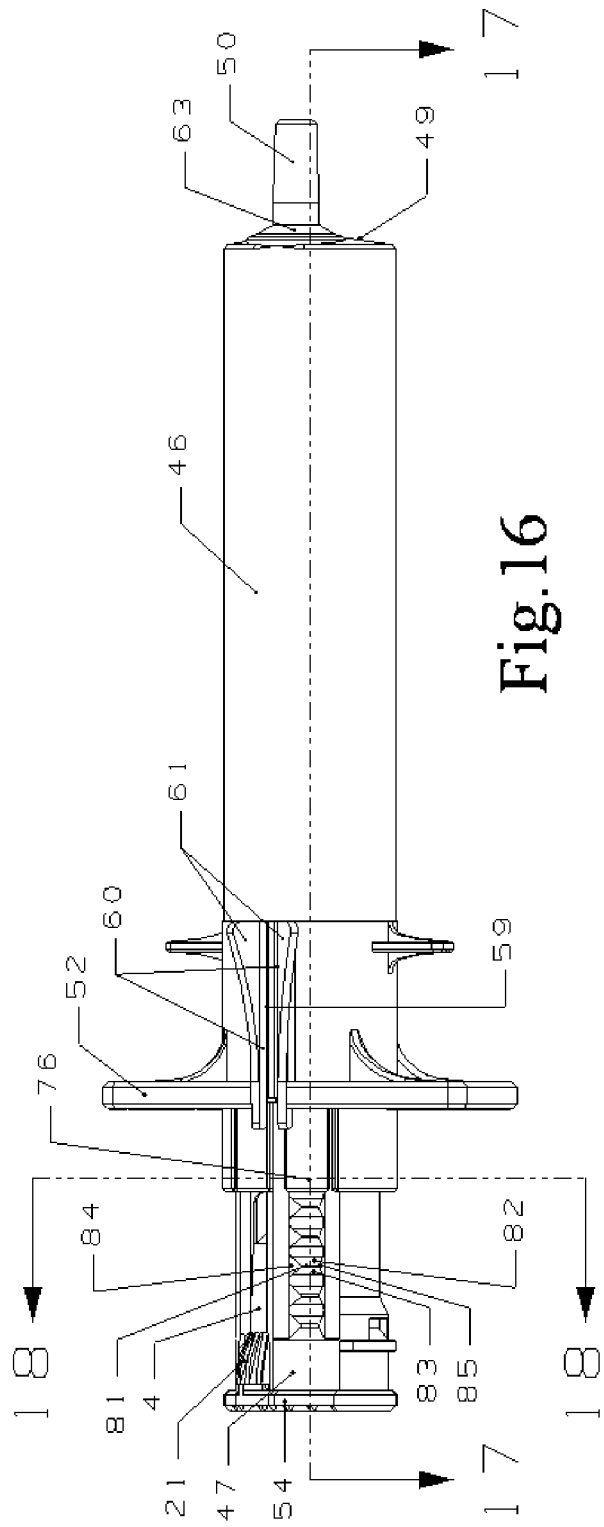
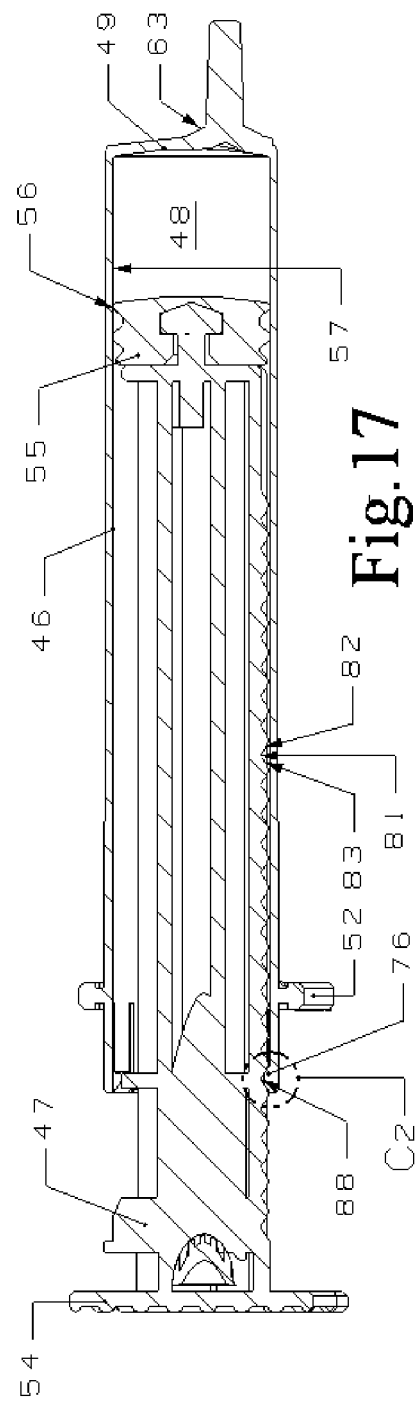
Fig.16
Fig.17

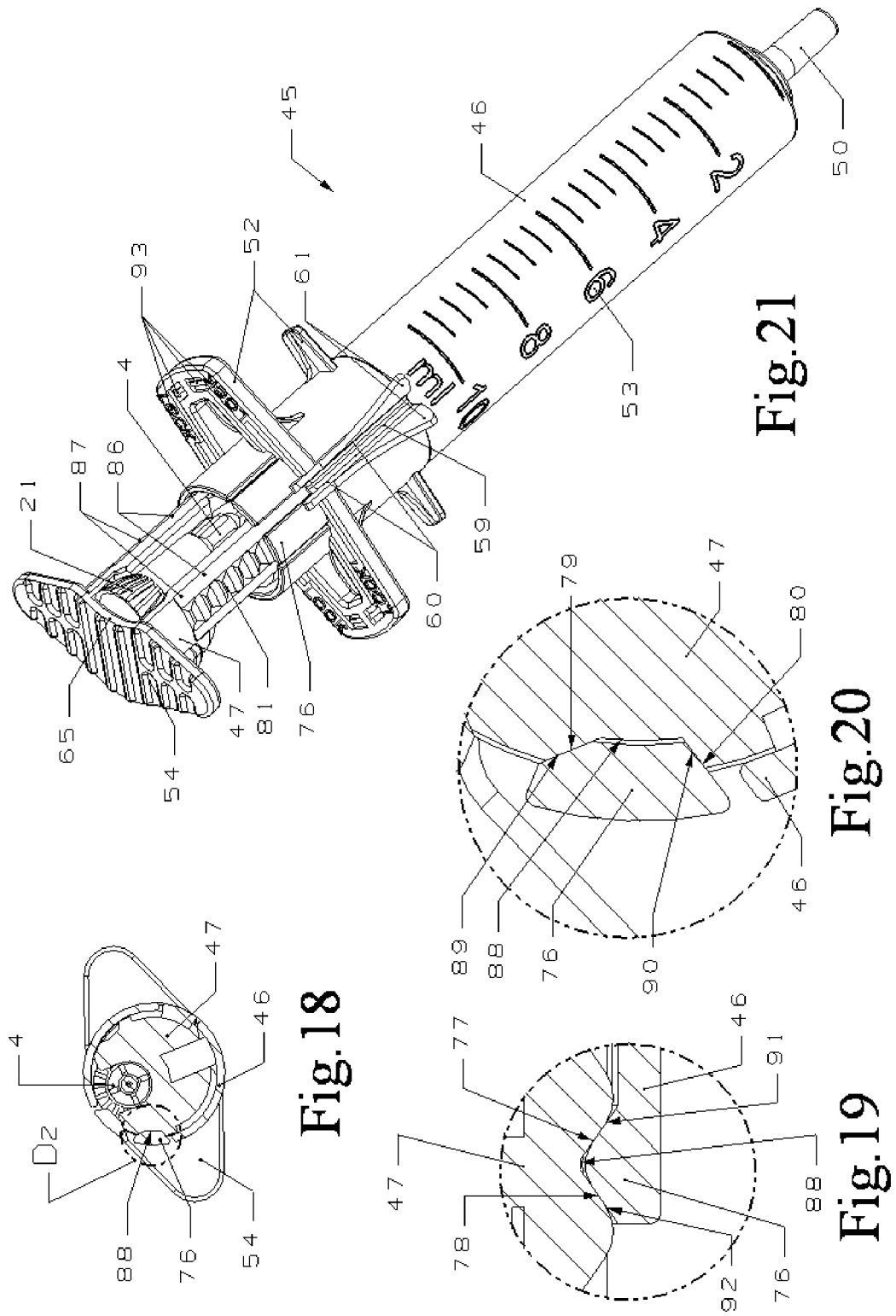

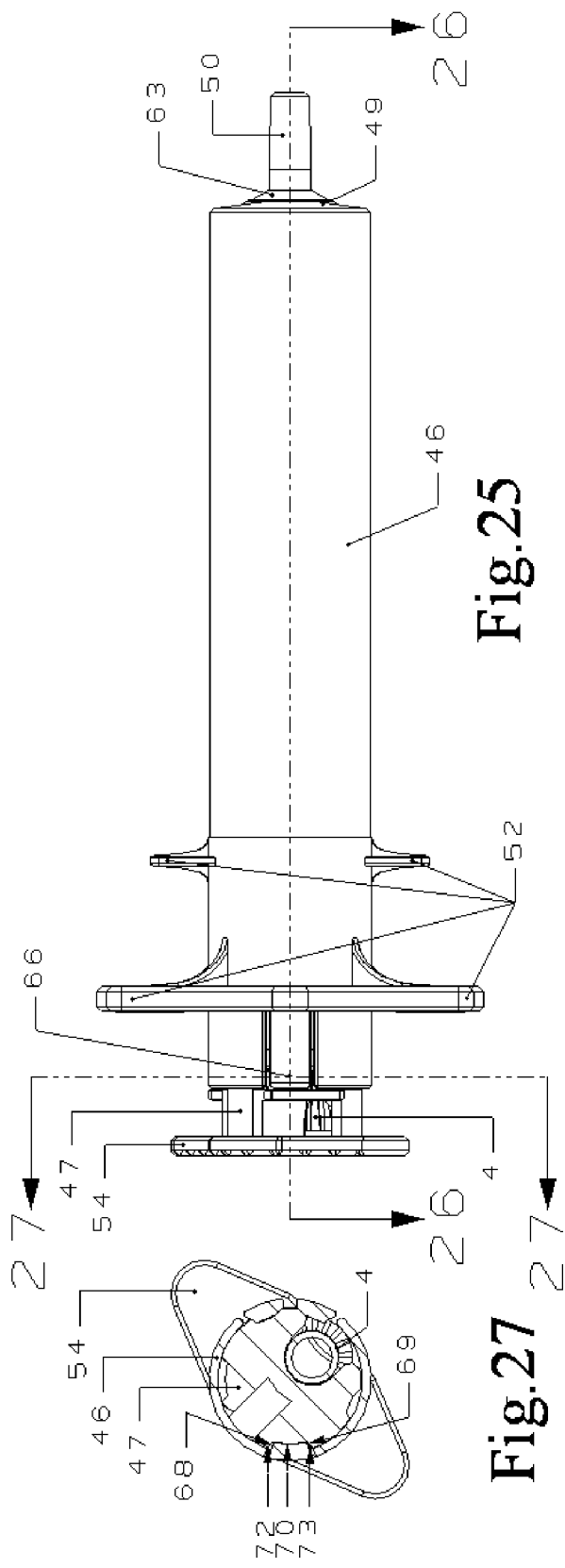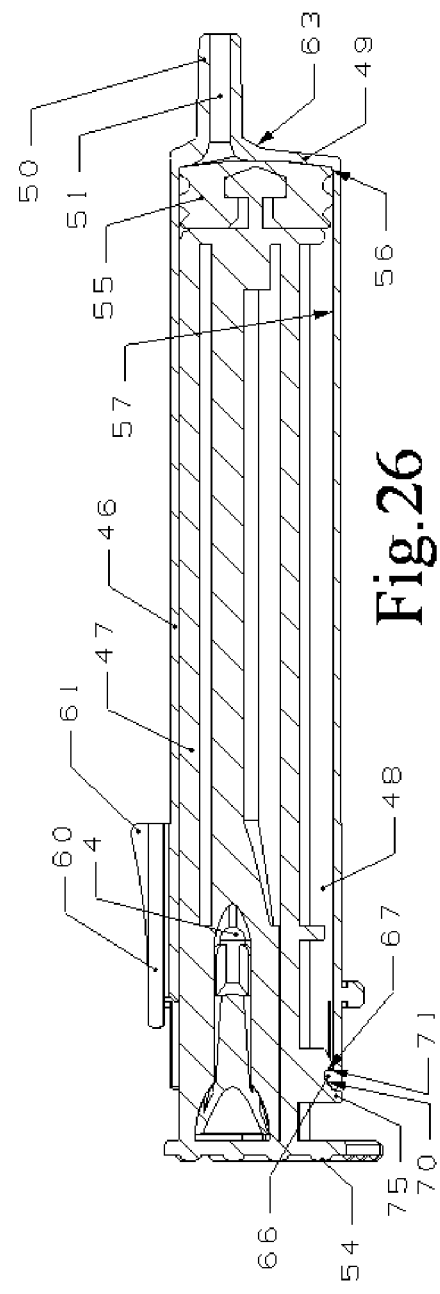

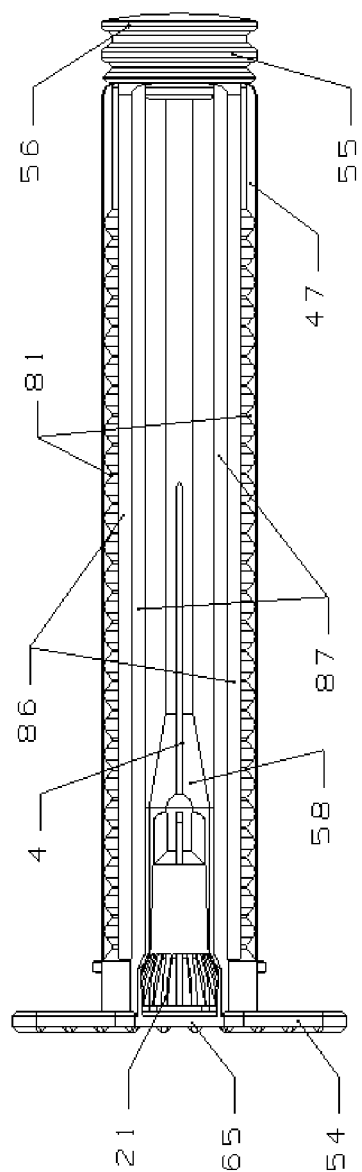
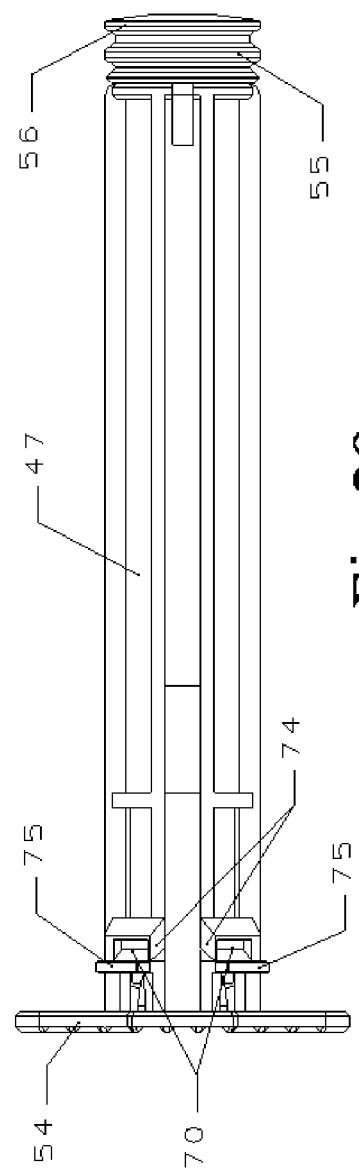
Fig.28
Fig.29

INTERFACE OF NEEDLE OF MEDICAL SYRINGE

CROSS REFERENCE TO RELATED PATENT APPLICATION

The present application is the US national stage of PCT/CN2017/109253 filed on Nov. 3, 2017, which claims the priorities of CN2017103455178 filed on May 16, 2017 and CN2017109677919 filed on Oct. 18, 2017, which applications are incorporated herein by reference.

BACKGROUND OF THE PRESENT INVENTION

Field of the Invention

The present invention relates to various medical syringes, specifically to various sterile syringes for single use, also specifically to various sterile syringes prefilled with medicine liquid for single use, more specifically to various sterile safety syringes for single use, and more specifically to various sterile safety syringes prefilled with medicine liquid for single use.

Description of Related Arts

Various medical syringes can be used to inject various liquids. They can also be used to mix various liquids or mix various liquids with powders. They can also be used to draw liquids, or mix various liquids, or mix liquids with powders in containers. They can also be used to flush objects. After the needle is plugged onto the conical fitting of medical syringe, various medical agents can be injected into the skin, muscle, blood vessel or other tissues and organs of the human body or animal, and various liquids can also be drawn from the tissues and organs of the human body or animal.

An existing conventional sterile syringe for single use includes a syringe barrel and a plunger rod. The syringe barrel is sufficiently transparent. The syringe barrel has a chamber. The chamber respectively has an opening at a front end and a proximal end of the syringe Nana A distal wall is provided at the front end of the chamber, A conical fitting is provided at a front end of the distal wall of the chamber. The conical fitting of the syringe barrel may be Luer slip centric or Luer slip excentric. The conical fitting has a passageway. The passageway joins the chamber through, A peripheral flange is provided at a rear part of the syringe barrel, A volume scale is provided at an outer surface of the syringe barrel, A thumbpress is provided at a proximal end of the plunger rod and a stopper is provided at a front part of the plunger rod. After the stopper of the plunger rod is plugged into the chamber from the opening in the proximal end of the chamber, the stopper is capable of moving forwards and backwards in the chamber by manipulating the thumbpress of the plunger rod, and an outer wall of the stopper and an inner wall of the chamber form a sealing fit of the sterile syringe for single use.

The first unsatisfactory aspect of the conventional sterile syringe for single use is that repeated use of the sterile syringe for single use can be harmful to human health after a sterile syringe for single use is used, the contaminated needle exposed is very easy to cause serious infection damage to the human body, and because the needle is tightly engaged with the conical fitting of the syringe barrel of the syringe, the actions of removing the contaminated needle and putting back the sleeve to close the needle head of the needle are the mostly highly dangerous actions that cause medical and healthcare personnel to be stabbed and wound by needles, A 2014 study sponsored by WHO, which focused on the most recent available data, estimated that in 2010, up to 1.7 million people were infected with hepatitis B virus, up to 315 000 with hepatitis C virus and as many as 33 800 with HIV through an unsafe injection, therefore, WHO is urging countries to transition, by 2020, to the exclusive use of the new "smart" syringes. The new injection safety guidelines and policies issued by WHO on Feb. 23, 2015 provide detailed recommendations suggesting that the new "smart" syringes WHO recommends for injections into the muscle or skin have features that prevent re-use, in addition, syringes are also being engineered with features to protect health workers from "needle stick" injuries and resulting infections. The second unsatisfactory aspect is that the sterile syringe for single use and the sheathed needle are placed separately in the package; the syringe needs to be taken out of the package during use, then sheathed needle is taken out of the package, then the sheath is removed and the needle is mounted on the syringe; after use, the needle needs to be removed from the syringe, and then the sheath is sought to cover the needle, or the sheath is directly used to cover the needle mounted on the syringe to prevent the naked needle from injuring the human body; the whole operation process is troublesome and it is easy to cause damage to users.

For various sterile safety syringes for single use described in U.S. patents US20120296277A1, US20150174339A1, US20150314079A1, US20160008554A1 and US20160271340A1, after use, various methods are adopted to collect the contaminated needle into the chamber of the sterile safety syringe for single use, so as to prevent the contaminated needle from seriously injuring the human body. The first unsatisfactory aspect of the above-mentioned sterile safety syringes for single use is that the parts of the sterile safety syringe for single use are more, more complex and more difficult to assemble than the conventional sterile syringe for single use. As a result, the production cost is much higher. The second unsatisfactory aspect of the above-mentioned various sterile safety syringes for single use is that a plurality of parts are provided in the liquid filling chamber of the sterile safety syringe for single use. It is difficult to completely exhaust the air in the liquid filling chamber of the sterile safety syringe for single use during liquid filling, such that air embolus will be caused in the blood vessel of the human body and a harm is caused to the human body. A third unsatisfactory aspect of the above-mentioned various sterile safety syringes for single use is that after the sterile safety syringe for single use is used, most part of the plunger rod stretch out of the syringe barrel, the overall volume after use is relatively large, which brings troubles to the subsequent destruction treatment. A fourth unsatisfactory aspect of the above-mentioned various sterile safety syringes for single use is that the needle of the sterile safety syringe for single use is in a clearance fit with the syringe barrel, and when the needle of the sterile safety syringe for single use pierce the muscle and blood vessel of the human body, the needle tip of the needle are liable to oscillate, causing misoperation.

It can be clearly seen from the above that the existing medical syringe needs to be further improved, such that the production cost of the medical syringe is lower, the medical syringe is safer and more convenient to use, and the medical syringe is more easily destroyed after use.

SUMMARY OF THE PRESENT INVENTION

The first purpose of the present invention is to provide a medical syringe and realize that a conical fitting and a conical inclined surface of a syringe barrel and a conical lip and a conical hole of a needle form an interface of the needle; when the conical hole of the needle is plugged onto the conical fitting of the syringe barrel, the needle is fixed onto the conical fitting of the syringe barrel to achieve the purpose of preventing a needle tip from swinging when the needle pierces a muscle or a blood vessel of a human body, so as to avoid misoperation; and after the medical syringe is used, the conical lip of the needle distal away from the needle tip only needs to be pinched flat, the needle can then be separated from the conical fitting of the syringe barrel of the medical syringe, and thus not only the contaminated needle can be put into a collection box, but also the contaminated needle can be collected into a catcher of a plunger rod of the medical syringe. The purpose of preventing contact with the needle tip in an operation process is achieved and thus the contaminated needle is prevented from injuring the human body.

The second purpose of the present invention is to provide a medical syringe and realize that one side of a plunger rod has a catcher with a side opening in which a needle can be put, and a thumbpress of the plunger rod has a notch in one side of the catcher; before the medical syringe is used, the needle is put into the catcher of the plunger rod; when the medical syringe is used, the conical lip of the needle which is put into the catcher of the plunger rod is nipped at the notch of the thumbpress of the plunger rod, and the needle is taken out of the side opening of the catcher; after the medical syringe is used, and after the needle plugged onto the conical fitting of the syringe barrel is taken down, then the needle is put into the catcher of the plunger rod from the side opening of the catcher, and then the plunger rod is pushed to the end such that most part of the plunger rod enters the syringe barrel, so as to achieve the purpose that the overall volume of the finally formed medical syringe is smaller, thereby facilitating subsequent destruction treatment.

The third purpose of the present invention is to provide a medical syringe and realize that a plunger rod has a catcher with a side opening in which a needle can be put; at a rear part of an outer wall of the syringe barrel, an axial needle guide groove is provided on the same side of the catcher of the plunger rod, there is respectively a wing obliquely extending towards both sides of the needle guide groove on an outer side of a rib on both sides of the needle guide groove. After the needle plugged onto the conical fitting of the syringe barrel is taken down, a needle tip is moved backwards along the needle guide groove, the wings on the both sides of the needle guide groove facilitate introducing the needle tip into the needle guide groove, and the ribs on the both sides of the needle guide groove prevent the needle tip from sliding out of the needle guide groove when moving backwards along the needle guide groove till the needle enters the catcher of the plunger rod from the side opening of the catcher of the plunger rod. The purpose of preventing contact with the needle tip in an operation process is achieved, and thus the contaminated needle is prevented from seriously injuring the human body.

The fourth purpose of the present invention is to provide a medical syringe and realize that an inward locking circumferential wedge is provided at a rear part of the chamber, a locking circumferential groove is provided at a periphery of the plunger rod, a circumferential protection wedge is provided at a proximal end of the locking circumferential groove of the plunger rod, and the locking circumferential wedge in the chamber is capable of being elastically deformed to cross the locking circumferential wedge of the plunger rod and enter the locking circumferential groove of the plunger rod; realize that a locking mark is provided on a rear side surface of the peripheral flange of the syringe barrel; realize that the plunger rod has a catcher with a side opening in which the needle can be put, and the thumbpress of the plunger rod has a notch in the side of the catcher; and realize that a conical fitting and a conical inclined surface of the syringe barrel and a conical lip and a conical hole of the needle form an interface of the needle. After the medical syringe is used, the conical lip of the needle distal away from the needle tip is pinched flat, the needle then can be separated from the conical fitting of the syringe barrel of the medical syringe, and not only can the contaminated needle be put into a collection box, but also the contaminated needle can enter the catcher of the plunger rod from the side opening of the catcher of the plunger rod, then, the plunger rod is pushed to the end, and then the plunger rod is rotated according a direction indicated by the locking mark such that the locking circumferential wedge in the chamber is elastically deformed to cross the locking axial wedge of the plunger rod and enter the locking circumferential groove of the plunger rod, and the plunger rod and the needle in the catcher of the plunger rod is thus locked in the chamber, and at this moment, the circumferential protection wedge covers the proximal end of the locking circumferential wedge in the chamber to prevent the locking circumferential wedge of the chamber which has already entered the locking circumferential groove of the plunger rod from being artificially pulled off the locking circumferential groove of the plunger rod. It not only achieves the purpose of preventing contact with the needle tip in the operation process, but also achieves the purpose that the overall volume of the finally formed medical syringe is smaller, and thus not only the contaminated needle can be prevented from seriously injuring the human body, but also reuse can be avoided and convenience can be brought to the subsequent destruction treatment.

The fifth purpose of the present invention is to provide a medical syringe and realize that an inward positioning circumferential wedge is provided at a rear part of the chamber, and there is a positioning axial wedge and a plurality of positioning circumferential grooves arranged and distributed along an axial direction of the plunger rod at a periphery of the plunger rod. After the plunger rod is rotated such that the positioning circumferential wedge in the chamber is elastically deformed to cross the positioning axial wedges of the plunger rod and enter a selected positioning circumferential groove of the plunger rod, a chamber between the stopper of the plunger rod constrained in the chamber and the distal wall of the chamber forms a selected liquid filling volume of the medical syringe; and after the plunger rod is rotated such that the positioning circumferential wedge in the chamber is elastically deformed to cross the positioning circumferential groove of the plunger rod and be removed out of the positioning circumferential groove of the plunger rod, the stopper is capable of moving forwards and backwards in the chamber by manipulating the thumbpress of the plunger rod. The purpose that the liquid filling amount of the medical syringe can be accurately locked is achieved.

The sixth purpose of the present invention is to provide a medical syringe and realize that the parts of the sterile safety syringe for single use of the present invention have one less part, i.e., a sheath of a needle, than the conventional sterile syringe for single use; and realize that the structure of the liquid filing chamber of the sterile safety syringes for single use of the present invention is the same as the structure of the conventional sterile syringe for single use. The sterile safety syringe for single use of the present invention not only achieves the purposes of facilitating exhausting gas in the liquid filling chamber and facilitating assembly, but also achieves the purpose that the production cost is almost the same as the production cost of the conventional sterile syringe for single use and lower than the production cost of the existing sterile safety syringe for single use.

The purposes of the present invention are implemented through the following technical solutions.

The medical syringe of the present invention includes a syringe barrel and a plunger rod. The syringe barrel is sufficiently transparent. The syringe barrel has a chamber. The chamber is respectively provided with an opening at a front end and a proximal end of the syringe barrel. A distal wall is provided at the front end of the chamber. A conical fitting is provided at a front end of the distal wall of the chamber. The conical fitting of the syringe barrel may be Luer slip centric or Luer slip excentric. The conical fitting has a passageway. The passageway joins the chamber through, A peripheral flange is provided at a rear part of the syringe barrel. A volume scale is provided at an outer surface of the syringe barrel, A thumbpress is provided at a proximal end of the plunger rod and a stopper is provided at a front part of the plunger rod. The stopper and the plunger rod may be made in an integral type and may also be made in a partable type. After the stopper of the plunger rod is plugged into the chamber from the opening in the proximal end of the chamber, the stopper is capable of moving forwards and backwards in the chamber by manipulating the thumbpress of the plunger rod. An outer wall of the stopper and an inner wall of the chamber form a sealing fit of the medical syringe.

The needle is capable of being plugged onto the conical fitting of the syringe barrel, A conical inclined surface is provided at a proximal end of the conical fitting of the syringe barrel, A conical lip and a conical hole are provided at a rear part of the needle. The conical lip of the needle is located at a rear part of the conical hole, Axial grooves may be distributed in a wall of the conical lip of the needle. A generatrix of the conical shape of the conical lip may be a straight line and may also be a curved line. The conical fitting and the conical inclined surface of the syringe barrel and the conical lip and the conical hole of the needle form an interface of the needle. When the conical hole of the needle is plugged onto the conical fitting of the syringe barrel, the needle is fixed onto the conical fitting of the syringe barrel. When the conical lip of the needle is pinched flat, the conical lip moves along the conical inclined surface of the proximal end of the conical fitting of the syringe barrel, such that the conical lip drives the needle to move forwards to enable the conical hole of the needle to be separated from the conical fitting of the syringe barrel.

A catcher with a side opening is provided on one side of the plunger rod of the medical syringe provided by the present invention. The needle can be put in the catcher. An in-cavity circumferential groove is provided at a proximal end of the catcher. The circumferential width of the side opening of the in-cavity circumferential groove of the catcher is smaller than the diameter of the conical lip of the needle and the diameter of the in-cavity circumferential groove of the catcher. When the needle is put into the catcher of the plunger rod, the conical lip of the needle is elastically deformed to cross the side opening of the in-cavity circumferential groove of the catcher and enter the in-cavity circumferential groove of the catcher, such that the conical lip of the needle is constrained in the in-cavity circumferential groove of the catcher and the needle is constrained in the catcher.

The thumbpress of the plunger rod has a notch on the side of the catcher. Before the medical syringe is used, the needle is put into the catcher of the plunger rod. When the medical syringe is used, the conical lip of the needle which is put into the catcher of the plunger rod is nipped at the notch of the thumbpress of the plunger rod, then the needle is taken out of the side opening of the catcher, and then the conical hole of the needle is plugged onto the conical fitting of the syringe barrel such that the needle is fixed onto the conical fitting of the syringe barrel.

After the medial syringe is used, the needle plugged onto the conical fitting of the syringe barrel may be taken down and the needle is put into the catcher of the plunger rod from the side opening of the catchier.

At a rear part of an outer wall of the syringe barrel, an axial needle guide groove is provided on the same side of the catcher of the plunger rod, An axial rib is provided on both sides of the needle guide groove respectively. A wing obliquely extending towards the both sides of the needle guide groove is respectively provided on an outer side of the rib. For the height obliquely extended by the wing, not only may the height of the front part be the same as the height of the rear part, but also the height of the front part may be greater than the height of the rear part. The ribs on the both sides of the needle guide groove and the outer wall of the syringe barrel form the needle guide groove. After the needle plugged onto the conical fitting of the syringe barrel is taken down, a needle tip is moved backwards along the needle guide groove, the wing on the both sides of the needle guide groove facilitates introducing the needle tip into the needle guide groove, and the ribs on the both sides of the needle guide groove prevent the needle tip from sliding out of the needle guide groove when moving backwards along the needle guide groove till the needle enters the catcher of the plunger rod from the side opening of the catcher of the plunger rod.

The syringe barrel has a side opening corresponding to the position of the catcher of the plunger rod in a rear part of the needle guide groove. After the needle plugged onto the conical fitting of the syringe barrel is taken down, the needle tip is moved backwards to the side opening of the syringe barrel along the needle guide groove such that the needle enters the catcher of the plunger rod from the side opening of the catcher of the plunger rod.

An inward locking circumferential wedge is provided at a rear part of the chamber of the medical syringe of the present invention. A wedge's axial constraint inclined surface is provided in an axial direction of the locking circumferential wedge. A wedge's circumferential constraint inclined surface is respectively provided on both sides of a circumferential direction of the locking circumferential wedge. A locking circumferential groove is provided at a periphery of the plunger rod. A groove's axial constraint inclined surface is provided in an axial direction of the locking circumferential groove. A groove's circumferential constraint inclined surface is respectively provided on both sides of a circumferential direction of the locking circumferential groove. A locking axial wedge is provided on a side surface of the circumferential direction of the locking circumferential groove. After the plunger rod is rotated such that the locking circumferential wedge in the chamber is elastically deformed to cross the locking axial wedge of the plunger rod and enter the locking circumferential groove of the plunger rod, the groove's axial constraint inclined surface of the locking circumferential groove of the plunger rod and the wedge's axial constraint inclined surface of the locking circumferential wedge in the syringe barrel constrain each other, and two said groove's circumferential constraint inclined surfaces of the locking circumferential groove of the plunger rod and two wedge's circumferential constraint inclined surfaces of the locking circumferential wedge in the chamber respectively constrain each other such that the plunger rod is locked on the chamber.

A block is provided at a front end between the two locking axial wedges of the plunger rod. When the plunger rod moves backwards to the opening in the proximal end of the chamber, the wedge's axial constraint inclined surface of the locking circumferential wedge of the chamber prevents the block of the plunger rod from farther moving backwards to prevent the plunger rod from being separated from the syringe barrel from the opening at the proximal end of the chamber.

A circumferential protection wedge is provided at a proximal end of the locking circumferential groove of the plunger rod. After the locking circumferential wedge in the chamber enters the locking circumferential groove of the plunger rod, the circumferential protection wedge covers a proximal end of the locking circumferential wedge in the chamber to prevent the locking circumferential wedge in the chamber which has already entered the locking circumferential groove of the plunger rod from being artificially pulled off the locking circumferential groove of the plunger rod.

A locking mark is provided on a rear side surface of the peripheral flange of the syringe barrel. After the plunger rod is rotated according to a direction indicated by the locking mark, the plunger rod is capable of being locked on the syringe barrel.

An inward positioning circumferential wedge is provided at a rear part of the chamber of the medical syringe of the present invention. Wedge's axial constraint inclined surfaces are respectively provided on both sides of an axial direction of the positioning circumferential wedge. Wedge's circumferential constraint inclined surfaces are respectively provided on both sides of a circumferential direction of the positioning circumferential wedge. The plurality of positioning circumferential grooves are provided at a periphery of the plunger rod. The plurality of positioning circumferential grooves are arranged and distributed along an axial direction of the plunger rod. Groove's axial constraint inclined surfaces are respectively provided on both sides of an axial direction of each positioning circumferential groove, A groove's circumferential constraint inclined surface is respectively provided on both sides of a circumferential direction of each positioning circumferential groove. A positioning axial wedge is provided on a side surface of a circumferential direction of the positioning circumferential groove. A wedge's circumferential constraint inclined surface is provided on a side surface of a circumferential direction of the positioning axial wedge. After the plunger rod is rotated such that the positioning circumferential wedge in the chamber is elastically deformed to cross the wedge's circumferential constraint inclined surface of the positioning axial wedge of the plunger rod and enter a selected positioning circumferential groove of the plunger rod, two said groove's circumferential constraint inclined surfaces of the selected positioning circumferential groove of the plunger rod and two said wedge's circumferential constraint inclined surfaces of the positioning circumferential wedge in the chamber constrain each other to prevent the plunger rod from rotating in the chamber, and two groove's axial constraint inclined surfaces of the selected positioning circumferential groove of the plunger rod and the two wedge's axial constraint inclined surfaces of the positioning circumferential wedge in the chamber constrain each other to prevent the stopper of the plunger rod from moving forwards and backwards in the chamber, such that a chamber between a front end of the stopper of the plunger rod constrained in the chamber and the distal wall of the chamber forms a selected liquid filling volume of the medical syringe. After the plunger rod is rotated such that the positioning circumferential wedge in the chamber is elastically deformed to cross the groove's circumferential constraint inclined surface of the selected positioning circumferential groove of the plunger rod and be removed out of the selected positioning circumferential groove of the plunger rod, the wedge's circumferential constraint inclined surface of the positioning axial wedge of the plunger rod prevents the positioning circumferential wedge in the chamber from entering the positioning circumferential groove of the plunger rod, and the stopper is capable of moving forwards and backwards in the chamber by manipulating the thumbpress of the plunger rod.

BRIEF DESCRIPTION OF THE DRAWINGS

FIG. 4 illustrates a rear view of the medical syringe in FIG. 1 in a self-locked state;

FIG. 5 shows a cross-sectional view taken along line 5-5 of FIG. 4;

FIG. 6 shows a cross-sectional view taken along line 6-6 of FIG. 4;

FIG. 12 is a perspective view of a plunger rod of the medical syringe in FIG. 1;

FIG. 13 is a perspective view of a hack side of FIG. 12;

FIG. 14 is a perspective view of a needle of the medical syringe in FIG. 1;

FIG. 16 is a perspective view of a medical syringe in a state that medicine liquid has already been filled and in a direction facing to a positioning circumferential groove of a plunger rod according to embodiment 2 of the present invention;

FIG. 17 shows a cross-sectional view taken along line 17-17 of FIG. 16;

FIG. 18 shows a cross-sectional view taken along line 18-18 of FIG. 16;

FIG. 19 illustrates a partial enlarged view of an area C2 in FIG. 17;

FIG. 20 illustrates a partial enlarged view of an area D2 in FIG. 18;

FIG. 21 is a perspective view of the medical syringe in FIG. 16;

FIG. 22 is a perspective view of the medical syringe in FIG. 21 when a needle is to be taken out or has already been put in;

FIG. 23 is a perspective view of the medical syringe in FIG. 21 to be used;

FIG. 25 illustrates a rear view of the medical syringe in FIG. 21 in self-locked state;

FIG. 26 shows a cross-sectional view taken along line 26-26 of FIG. 25;

FIG. 27 shows a cross-sectional view taken along line 27-27 of FIG. 26;

FIG. 28 illustrates a front view when a needle in FIG. 21 is put into a plunger rod;

FIG. 29 illustrates a rear view of a plunger rod of the medical syringe in FIG. 21;

DETAILED DESCRIPTION OF THE PREFERRED EMBODIMENTS

Figure 1:
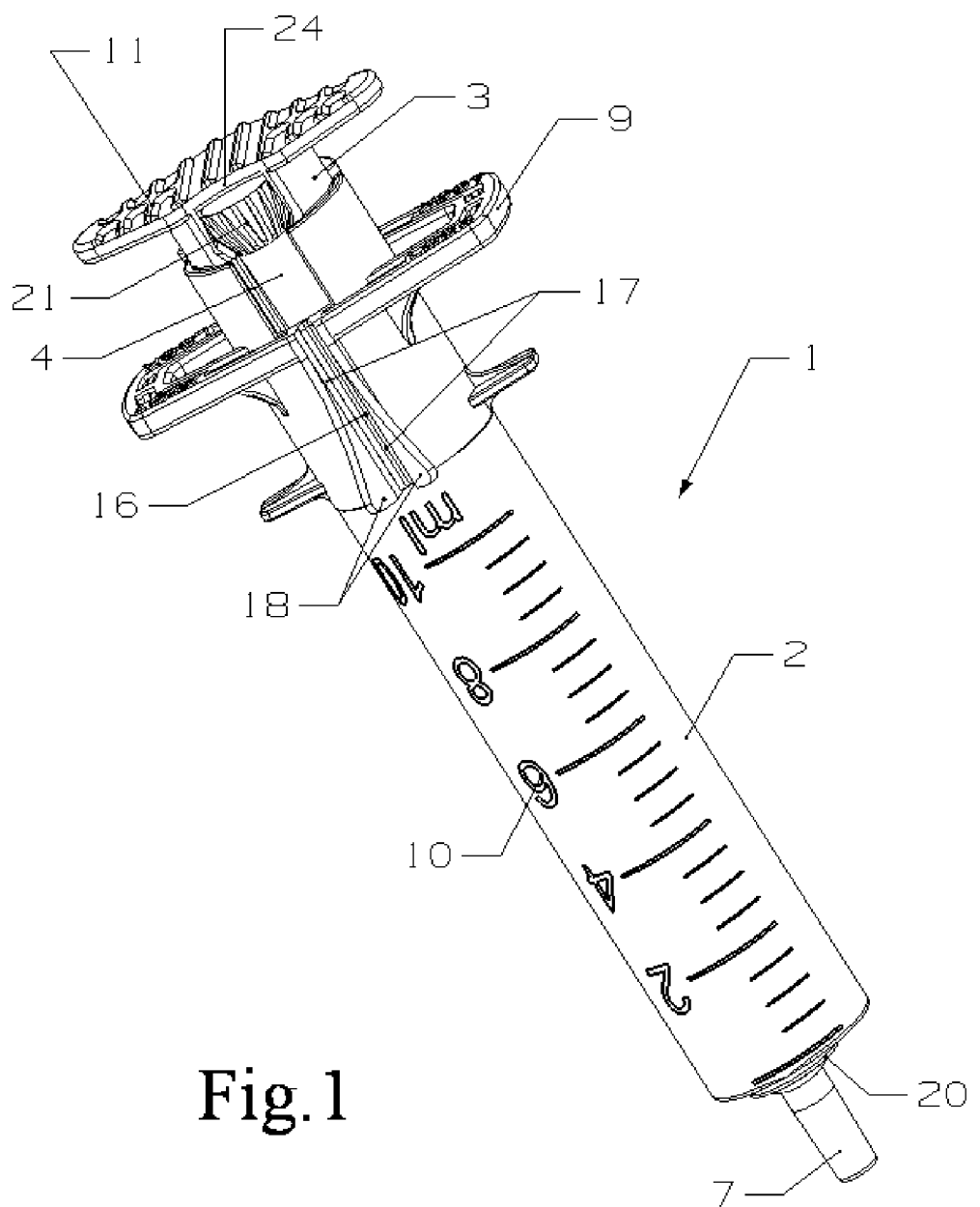
FIG. 1 is a perspective view of a medical syringe before use according to embodiment 1 of the present invention.

Exemplary embodiments of an interface of the needle of the medical syringe of the present invention are described using examples and with reference to the accompanying drawings. The scope of the present invention is subject to the claims. It should be noted that some or all of the accompanying drawings are simple drawings merely provided for illustrating the exemplary embodiments of the present invention. Therefore, actual sizes of the components are not show in the drawings. Practical methods for achieving the above and other objectives and advantages of the present invention can be better comprehended through detailed description of the exemplary embodiments.

In the accompanying drawings and following description, the terms "proximal" and "rear" refer to a position close to a manipulator of the medical syringe, and the terms "distal" and "front" refer to a position away from a manipulator of the medical syringe. The term "axial direction" takes a long axis direction of a syringe barrel of the medical syringe as a benchmark, and the term "circumferential direction" takes a circumference direction of a radial section of the syringe barrel of the medical syringe as a benchmark. The term "in" and "inward" refers to a position close to a long axis of the syringe barrel of the medical syringe, while the term "out" refers to a position distal away from the long axis of the syringe barrel of the medical syringe. The terms related to positions and directions may be further understood according to the accompanying drawings and the following description.

FIGS. 1-14 show a medical syringe 1 according to first embodiment of the present invention. The medical syringe 1 includes a syringe barrel 2, a plunger rod 3 and a needle 4 (refer to FIG. 1). The syringe barrel 2 (refer to FIG. 4, FIG. 5 and FIG. 10) has a chamber 5. The chamber 5 has an opening in a proximal end of the syringe barrel 2. A distal wall 6 is provided at a front end of the chamber 5. A conical fitting 7 is provided at a front end of the distal wall 6 of the chamber 5. The conical fitting 7 has a passageway 8. The passageway 8 joins the chamber 5 through. A peripheral flange 9 is provided at a rear part of the syringe barrel 2. A volume scale 10 is provided at an outer surface of the syringe barrel 2. A thumbpress 11 is provided at a proximal end of the plunger rod 3 (refer to FIG. 12 and FIG. 13) and a stopper 12 is provided at a front part of the plunger rod 3. After the stopper 12 of the plunger rod 3 is plugged into the chamber 5 from the opening in the proximal end of the chamber 5, the stopper 12 is capable of moving forwards and backwards in the chamber 5 by manipulating the thumbpress 11 of the plunger rod 3. An outer wall 13 of the stopper 12 and an inner wall 14 of the chamber 5 form a sealing fit of the medical syringe 1.

The plunger rod 3 has a catcher 15 with a side opening (refer to FIG. 12). At a rear part of an outer wall of the syringe barrel 2, an axial needle guide groove 16 (refer to FIG. 10) is provided on the same side of the catcher 15 of the plunger rod 3. An axial rib is provided on both sides of the needle guide groove 16 respectively. A wing 18 obliquely extending towards both sides of the needle guide groove 16 is respectively provided on an outer side of the rib 17. The height of the obliquely extending front part of the wing 18 is greater than the height of the rear part. The ribs 17 on the both sides of the needle guide groove 16 and the outer wall of the syringe barrel 2 form the needle guide groove 16. The syringe barrel 2 has a side opening 19 corresponding to the position of the catcher 15 of the plunger rod 3 in a rear part of the needle guide groove 16. After the needle 4 plugged onto the conical fitting 7 of the syringe barrel 2 is taken down, a needle tip of the needle 4 is moved backwards to the side opening 19 of the syringe barrel 2 along the needle guide groove 16 such that the needle 4 enters the catcher 15 of the plunger rod 3 from the side opening of the catcher 15 of the plunger rod 3 (refer to FIG. 3). The wing 18 on the both sides of the needle guide groove 16 facilitates introducing the needle tip of the needle 4 into the needle guide groove 16. The ribs 17 on the both sides of the needle guide groove 16 prevent the needle tip of the needle 4 from sliding out of the needle guide groove 16 when moving backwards along the needle guide groove 16.

Figure 2:
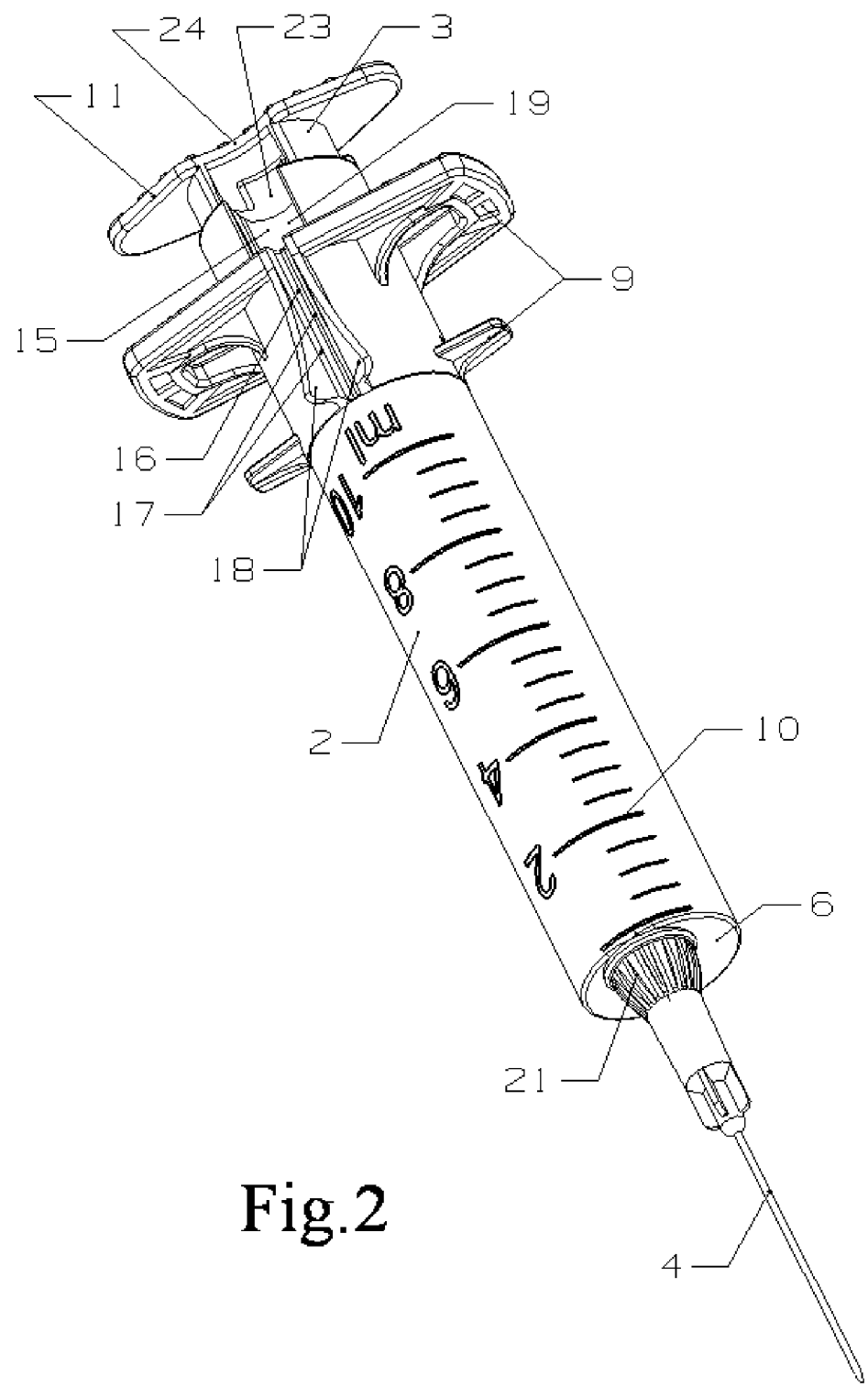
FIG. 2 is a perspective view of the medical syringe in FIG. 1 to be used.
Figure 3:
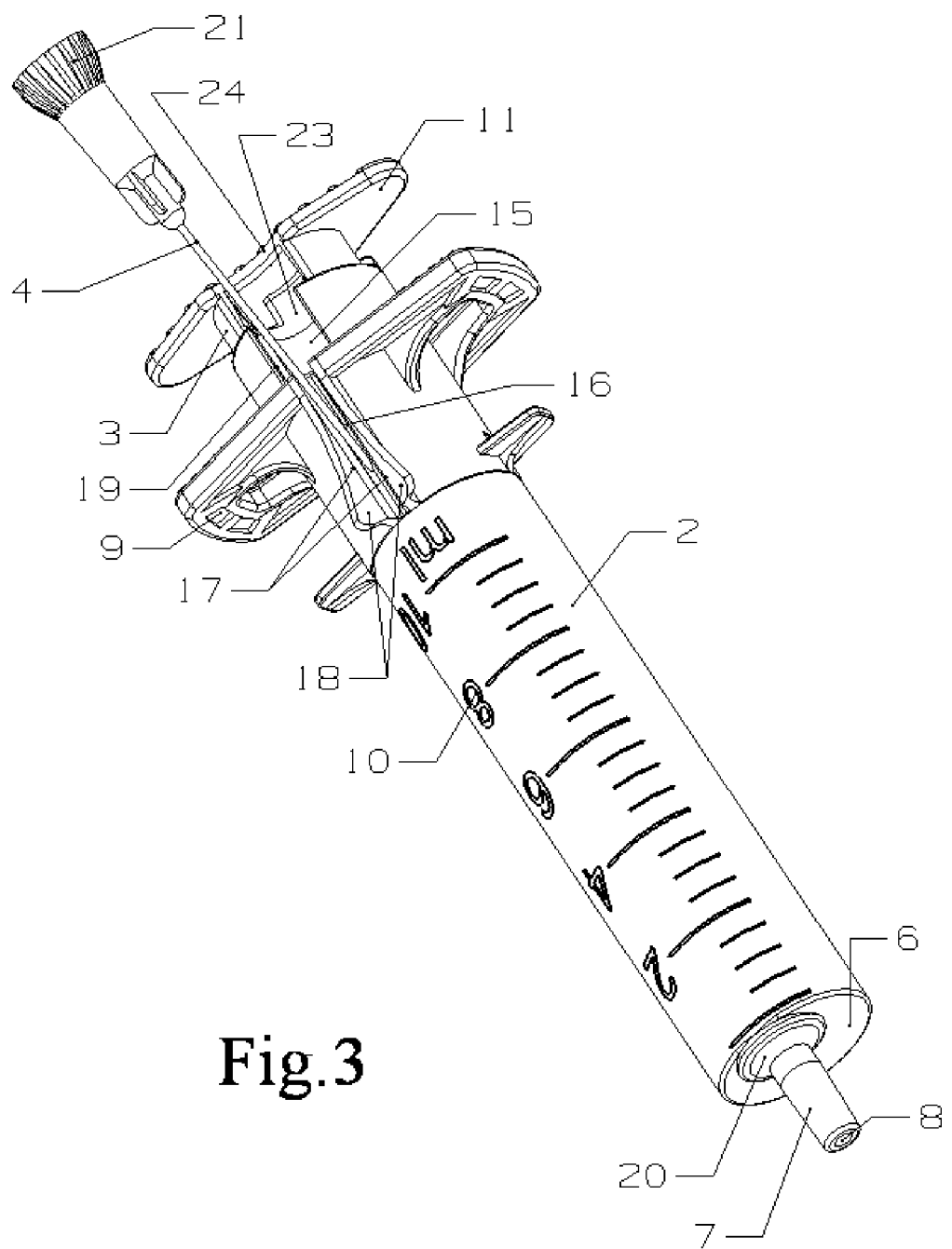
FIG. 3 is a perspective view of the medical syringe after use when a needle tip moves along a needle guide groove.

A conical inclined surface 20 is provided at a proximal end of the conical fitting 7 of the syringe barrel 2 (refer to FIG. 3). A conical lip 21 and a conical hole 22 are provided at a rear part of the needle 4 (refer to FIG. 14). The conical lip 21 of the needle 4 is located at a rear part of the conical hole 22. An in-cavity circumferential groove 23 is provided at a proximal end of the catcher 15 of the plunger rod 3 (refer to FIG. 12). The circumferential width of the side opening of the in-cavity circumferential groove 23 of the catcher 15 of the plunger rod 3 is smaller than the diameter of the conical lip 21 of the needle 4 and the diameter of the in-cavity circumferential groove 23 of the catcher 15. When the needle 4 is put into the catcher 15 of the plunger rod 3 (refer to FIG. 11), the conical lip 21 of the needle 4 is elastically deformed to cross the side opening of the in-cavity circumferential groove 23 of the catcher 15 and enter the in-cavity circumferential groove 23 of the catcher 15, such that the conical lip 21 of the needle 4 is constrained in the in-cavity circumferential groove 23 of the catcher 15 and the needle 4 is constrained in the catcher 15. When the conical hole 22 of the needle 4 is plugged onto the conical fitting 7 of the syringe barrel 2 (refer to FIG. 2), the needle 4 is fixed onto the conical fitting 7 of the syringe barrel 2.

When the conical lip 21 of the needle 4 is pinched flat, the conical lip 21 moves along the conical inclined surface 20 of the proximal end of the conical fitting 7 of the syringe barrel 2, such that the conical lip 21 drives the needle 4 to move forwards to enable the conical hole 22 of the needle 4 to be separated from the conical fitting 7 of the syringe barrel 2.

The thumbpress 11 of the plunger rod 3 has a notch 24 on the side of the catcher 15 (refer to FIG. 1 and FIG. 2). Before the medical syringe 1 is used, the needle 4 is put into the catcher 15 of the plunger rod 3 (refer to FIG. 1). When the medical syringe 1 is used, the conical lip 21 of the needle 4 which is put into the catcher 15 of the plunger rod 3 is nipped at the notch 24 of the thumbpress 11 of the plunger rod 3, then the needle 4 is taken out of the side opening of the catcher 15, and then the conical hole 22 of the needle 4 is plugged onto the conical fitting 7 of the syringe barrel 2 such that the needle 4 is fixed onto the conical fitting 7 of the syringe barrel 2 (refer to FIG.

An inward locking circumferential wedge 25 is provided at a rear part of the chamber 5 (refer to FIG. 4 to FIG. 9 and FIG. 10). A large-inclination-angle wedge's axial constraint inclined surface 26 is provided in an axial direction of the locking circumferential wedge 25. Large-inclination-angle wedge's circumferential constraint inclined surfaces 27 and 28 are provided on both sides of a circumferential direction of the locking circumferential wedge 25 respectively. A locking circumferential groove 29 is provided at a periphery of the plunger rod 3 (refer to FIG. 4 to FIG. 9 and FIG. 13). A large-inclination-angle groove's axial constraint inclined surface 30 is provided in an axial direction of the locking circumferential groove 29. Large-inclination-angle groove's circumferential constraint inclined surfaces 31 and 32 are provided on both sides of a circumferential direction of the locking circumferential groove 29 respectively. A locking axial wedge 33 is provided on a side surface of the circumferential direction of the locking circumferential groove 29. When the medical syringe 1 is used, the locking axial wedge 33 of the plunger rod 3 prevents the locking circumferential wedge 25 in the chamber 5 from crossing the locking axial wedge 33 of the plunger rod 3 and entering the locking circumferential groove 29 of the plunger rod 3. After the medical syringe 1 is used and after the needle 4 plugged onto the conical fitting 7 of the syringe barrel 2 is taken down, the needle 4 is put into the catcher 15 of the plunger rod 3 (refer to FIG. 1), When the stopper 12 of the plunger rod 3 is located at the distal wall 6 of the syringe barrel 2 (refer to FIG. 1), the plunger rod 3 is rotated such that the locking circumferential wedge 25 in the chamber 5 is elastically deformed to cross the locking axial wedge 33 of the plunger rod 3 and enter the locking circumferential groove 29 of the plunger rod 3, the large-inclination-angle groove's axial constraint inclined surface 30 of the locking circumferential groove 29 of the plunger rod 3 and the large-inclination-angle wedge's axial constraint inclined surface 26 of the locking circumferential wedge 25 in the chamber 5 constrain each other to prevent the plunger rod 3 from moving forwards and backwards in the chamber 5, and the two large-inclination-angle groove's circumferential constraint inclined surfaces 31 and 32 of the locking circumferential groove 29 of the plunger rod 3 and the two large-inclination-angle wedge's circumferential constraint inclined surfaces 27 and 28 of the locking circumferential wedge 25 in the chamber 5 respectively constrain each other to prevent the plunger rod 3 from rotating in the chamber 5 (refer to FIG. 4 to FIG. 9); and at the same time, an audible sound made when the locking circumferential wedge 25 in the chamber 5 is elastically deformed prompts that the plunger rod 3 and the needle 4 which is put into the catcher 15 of the plunger rod 3 have already been locked in the syringe barrel 2 (refer to FIG. 9).

A circumferential protection wedge 34 is provided at a proximal end of the locking circumferential groove 29 of the plunger rod 3 (refer to FIG. 13). After the plunger rod 3 is rotated such that the locking circumferential wedge 25 in the chamber 5 is elastically deformed to cross the locking axial wedge 33 of the plunger rod 3 and enter the locking circumferential groove 29 of the plunger rod 3, the circumferential protection wedge 34 covers a proximal end of the locking circumferential wedge 25 in the chamber 5 (refer to FIG. 7 and FIG. 9) to prevent the locking circumferential wedge 25 in the chamber 5 which has already entered the locking circumferential groove 29 of the plunger rod 3 from being artificially pulled off the locking circumferential groove 29 of the plunger rod 3.

Figure 9:
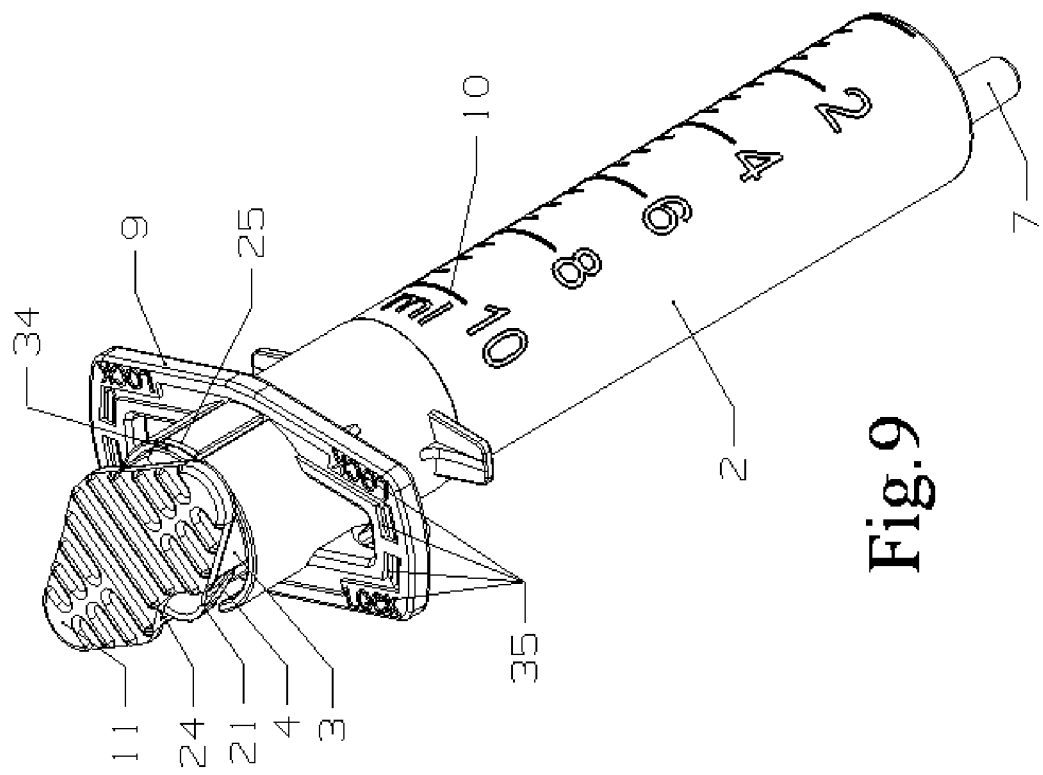
FIG. 9 is a perspective view of FIG. 4.
Figure 7:
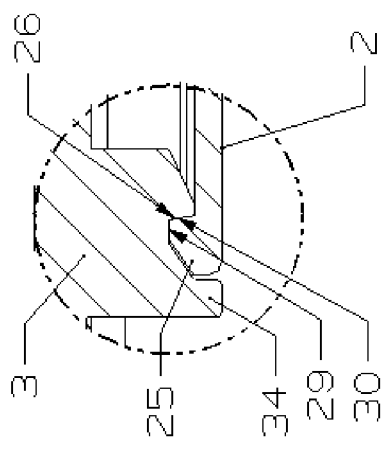
FIG. 7 illustrates a partial enlarged view of an area C1 in FIG. 5.
Figure 8:
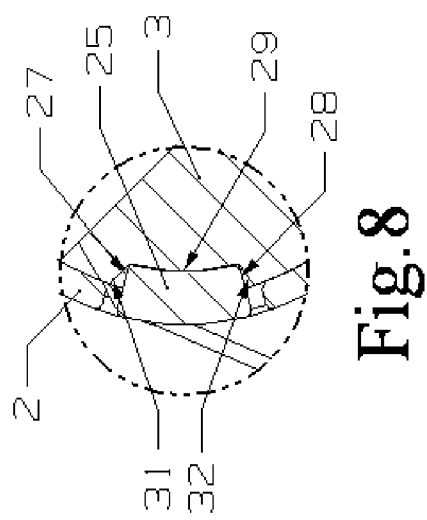
FIG. 8 illustrates a partial enlarged view of an area D1 in FIG. 6.
Figure 11:
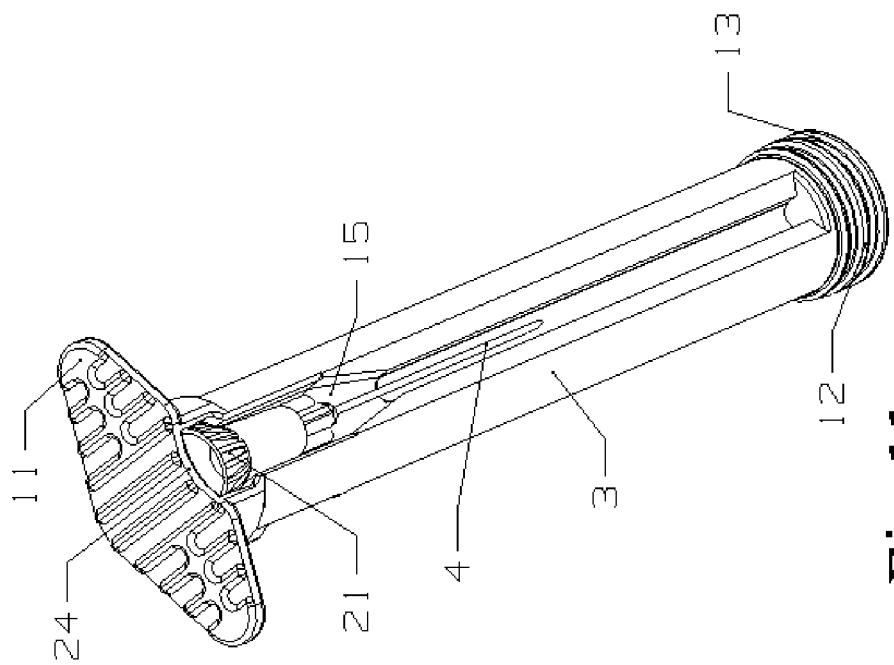
FIG. 11 is a perspective view when a needle is put into a plunger rod.
Figure 10:
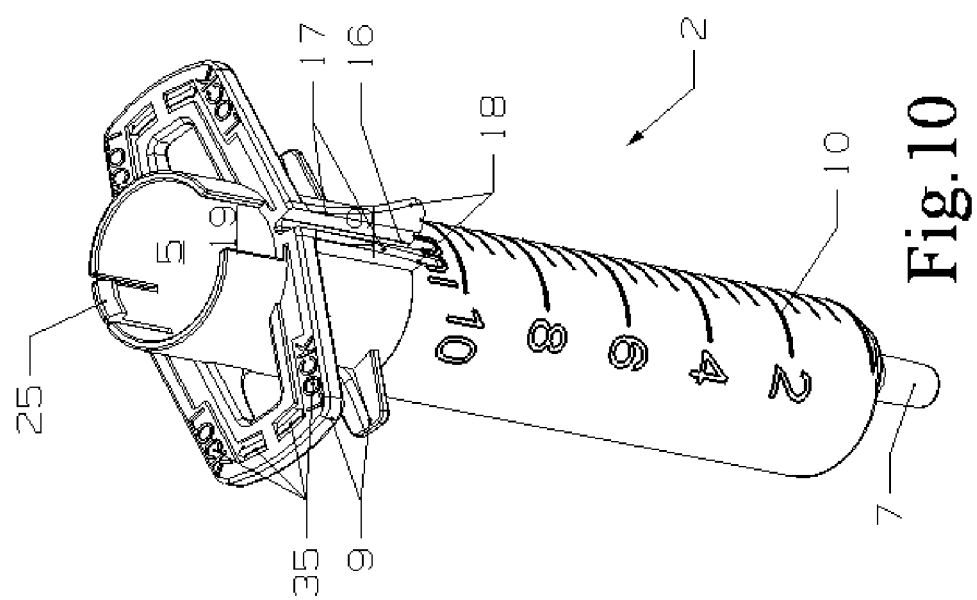
FIG. 10 is a perspective view of a syringe barrel of the medical syringe in FIG. 1.

A locking mark 35 is provided on a rear side surface of the peripheral flange 9 of the syringe barrel 2 (refer to FIG. 9 and FIG. 10). After the plunger rod 3 is rotated according to a direction indicated by the locking mark 35, the plunger rod 3 is capable of being locked on the syringe barrel 2.

A block 36 is provided at a front end between two locking axial wedges 33 of the plunger rod 3 (refer to FIG. 13). When the plunger rod 3 moves backwards to the opening at the proximal end of the chamber 5, the wedge's axial constraint inclined surface 26 of the locking circumferential wedge 25 of the chamber 5 prevents the block 36 of the plunger rod 3 from further moving backwards to prevent the plunger rod 3 from being separated from the syringe barrel 2 from the opening at the proximal end of the chamber 5.

Figure 15:
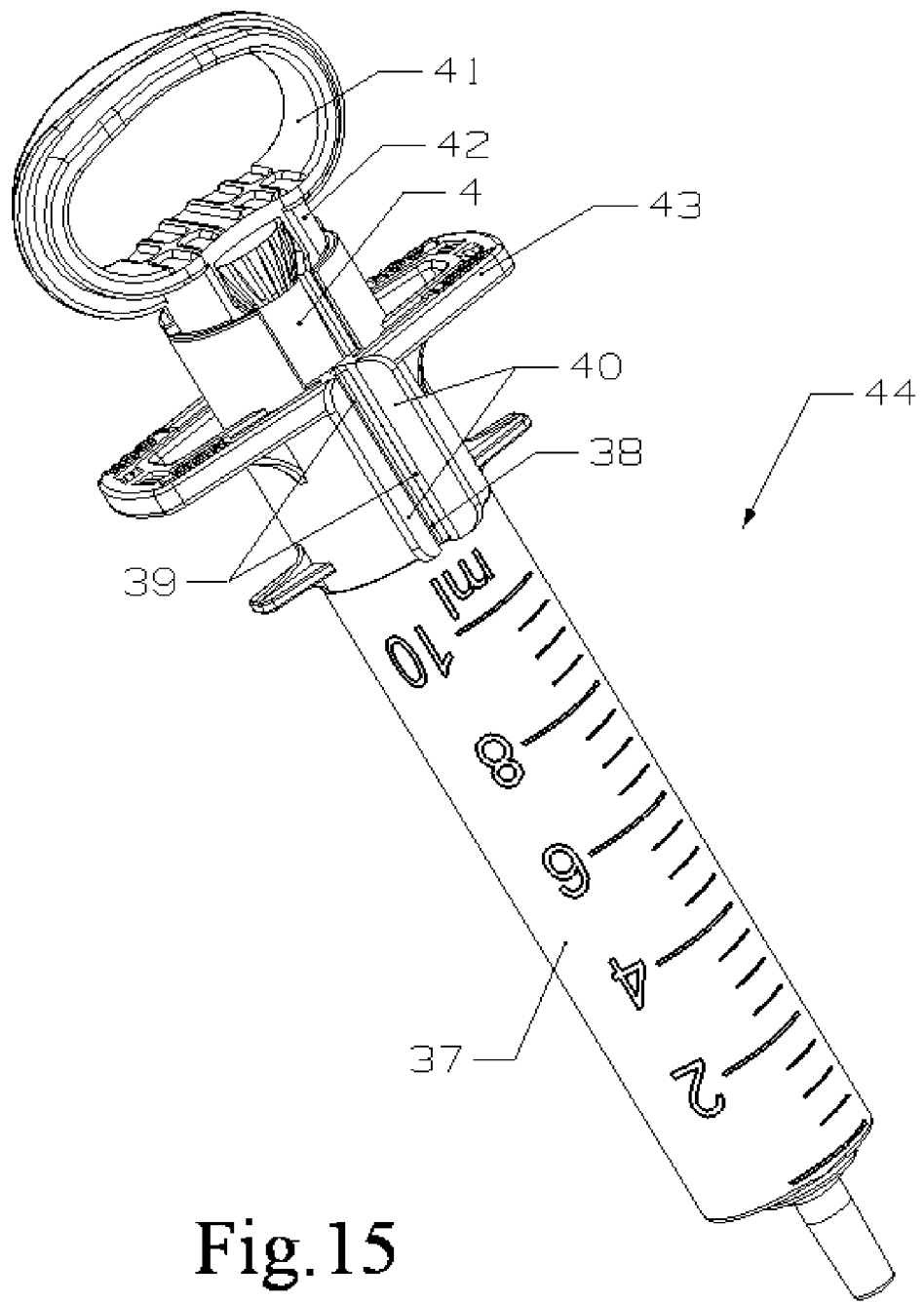
FIG. 15 is a perspective view of another medical syringe similar to the medical syringe in FIG. 1.
Figure 24:
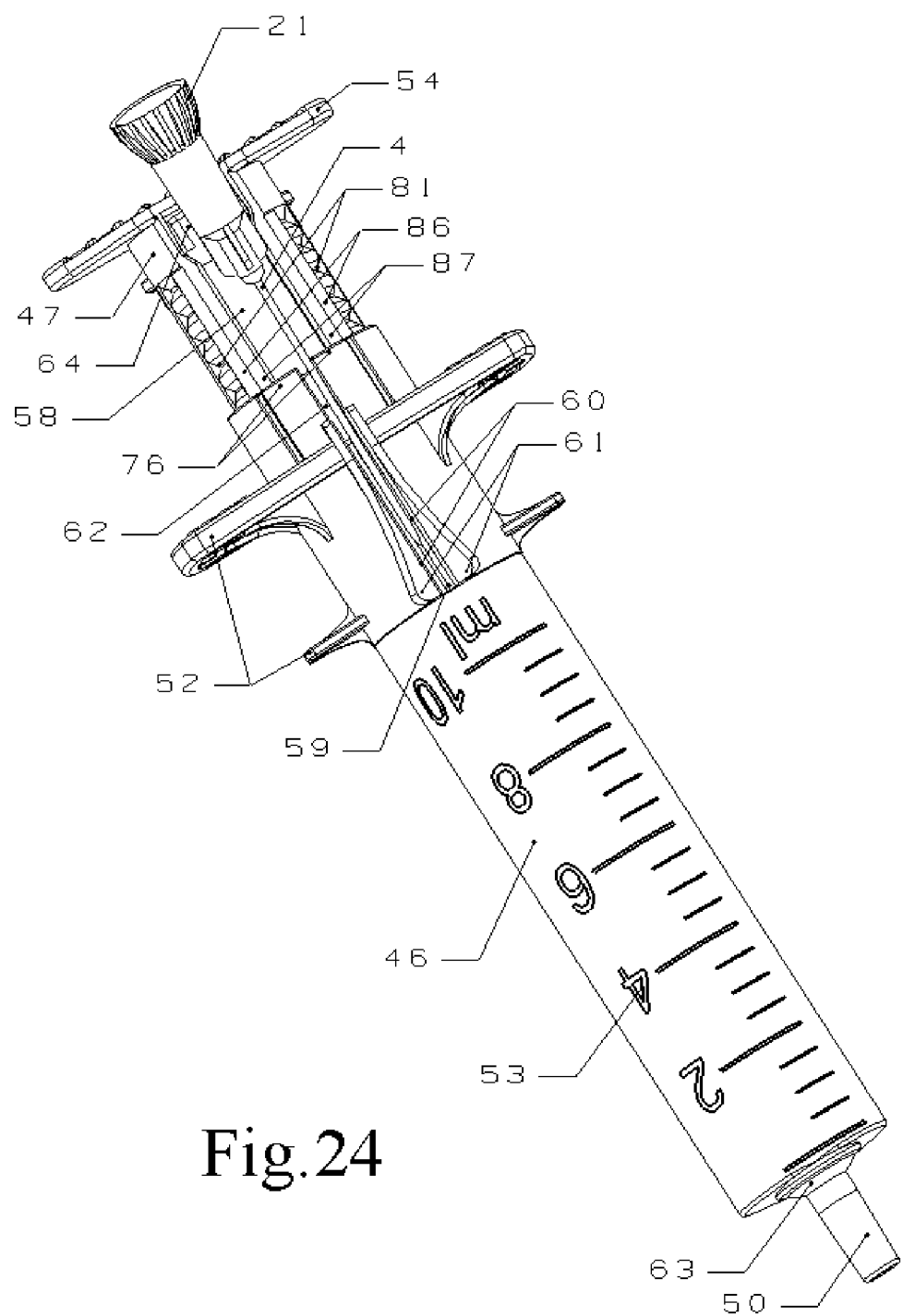
FIG. 24 is a perspective view of the medical syringe in FIG. 21 after use when a needle tip of a needle moves along a needle guide groove.

The syringe barrel 2 of the medical syringe 1 may also be replaced with a syringe barrel 37. The height of front parts of wings 40 obliquely extending towards both sides of ribs 39 on both sides of a needle guide groove 38 of the syringe barrel 37 is the same as the height of rear parts (refer to FIG. 15). The plunger rod 3 of the medical syringe 1 may also be replaced with a plunger rod 42 with an annular thumbpress 41 (refer to FIG. 15). The annular thumbpress 41 of the plunger rod 42 cooperates with a peripheral flange 43 of the syringe barrel 37 such that the medical syringe 44 can be more conveniently operated by a single hand.

FIGS. 16-31 show a medical syringe 45 prefilled with medicine liquid according to second embodiment of the present invention. The medical syringe 45 includes a syringe barrel 46, a plunger rod 47 and a needle 4 (refer to FIG. 21). The syringe barrel 46 (refer to FIG. 26, FIG. 30 and FIG. 31) has a chamber 48. The chamber 48 has an opening at a proximal end of the syringe barrel 46. A distal wall 49 is provided at a front end of the chamber 48. A conical fitting 50 is provided at a front end of the distal wall 49 of the chamber 48. The conical fitting 50 has a passageway 51. The passageway 51 joins the chamber 48 through. A peripheral flange 52 is provided at a rear part of the syringe barrel 46. A volume scale 53 is provided at an outer surface of the syringe barrel 46. A thumbpress 54 is provided at a proximal end of the plunger rod 47 (refer to FIG. 28 and FIG. 29) and a stopper 55 is provided at a front part of the plunger rod 47. After the stopper 55 of the plunger rod 47 is plugged into the chamber 48 from the opening in the proximal end of the chamber 48, the stopper 55 is capable of moving forwards and backwards in the chamber 48 by manipulating the thumbpress 54 of the plunger rod 47. An outer wall 56 of the stopper 55 and an inner wall 57 of the chamber 48 form a sealing fit of the medical syringe 45.

The plunger rod 47 has a catcher 58 with a side opening (refer to FIG. 28). At a rear part of an outer wall of the syringe barrel 46, an axial needle guide groove 59 (refer to FIG. 30) is provided on the same side of the catcher 58 of the plunger rod 47. An axial rib 60 is respectively provided on both sides of the needle guide groove 59. A wing 61 obliquely extending towards both sides of the needle guide groove 59 is respectively provided on an outer side of the rib 60. The height of the obliquely extending front part of the wing 61 is greater than the height of the rear part. The ribs 60 on the both sides of the needle guide groove 59 and the outer wall of the syringe barrel 46 form the needle guide groove 59. The syringe barrel 46 has a side opening 62 corresponding to the position of the catcher 58 of the plunger rod 47 in a rear part of the needle guide groove 59. After the needle 4 plugged onto the conical fitting 50 of the syringe barrel 46 is taken down, a needle tip of the needle 4 is moved backwards to the side opening 62 of the syringe barrel 46 along the needle guide groove 59 (refer to FIG. 24) such that the needle 4 enters the catcher 58 of the plunger rod 47 from the side opening of the catcher 58 of the plunger rod 47 (refer to FIG. 22). The wing 61 on the both sides of the needle guide groove 59 facilitates introducing the needle tip of the needle 4 into the needle guide groove 59. The ribs 60 on the both sides of the needle guide groove 59 prevent the needle tip of the needle 4 from sliding out of the needle guide groove 59 when moving backwards along the needle guide groove 59.

Figures 22, 23:
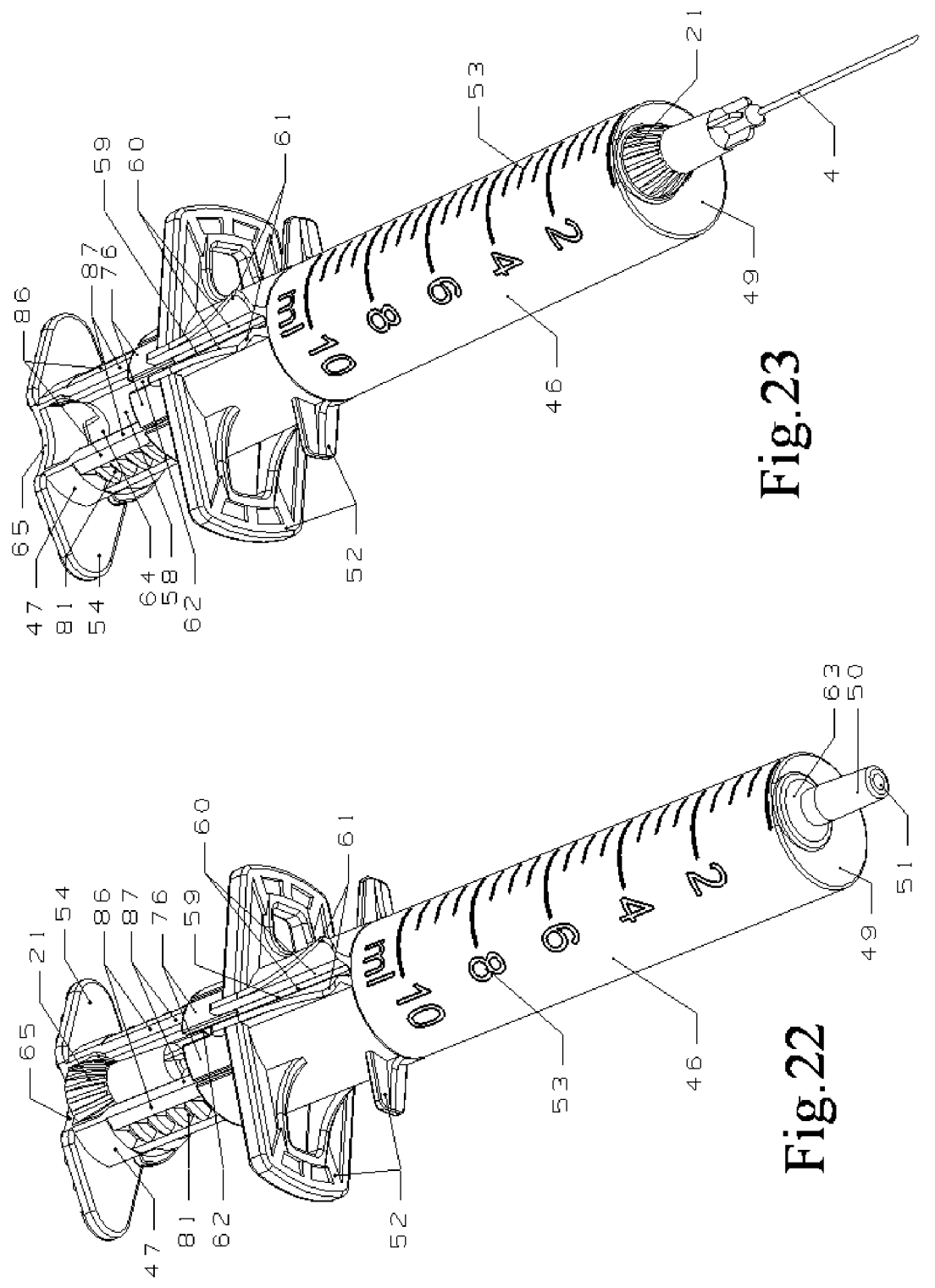

A conical inclined surface 63 is provided at a proximal end of the conical fitting 50 of the syringe barrel 46 (refer to FIG. 22). An in-cavity circumferential groove 64 is provided at a proximal end of the catcher 58 of the plunger rod 47 (refer to FIG. 23 and FIG. 28). The circumferential width of the side opening of the in-cavity circumferential groove 64 of the catcher 58 of the plunger rod 47 is smaller than the diameter of the conical lip 21 of the needle 4 and the diameter of the in-cavity circumferential groove 64 of the catcher 58, When the needle 4 is put into the catcher 58 of the plunger rod 47 (refer to FIG. 22 and FIG. 28), the conical lip 21 of the needle 4 is elastically deformed to cross the side opening of the in-cavity circumferential groove 64 of the catcher 58 and enter the in-cavity circumferential groove 64 of the catcher 58, such that the conical lip 21 of the needle 4 is constrained in the in-cavity circumferential groove 64 of the catcher 58 and the needle 4 is constrained in the catcher 58, When the conical hole 22 of the needle 4 is plugged onto the conical fitting 50 of the syringe barrel 46 (refer to FIG. 23), the needle 4 is fixed onto the conical fitting 50 of the syringe barrel 46. When the conical lip 21 of the needle 4 is pinched flat, the conical lip 21 moves along the conical inclined surface 63 of the proximal end of the conical fitting 50 of the syringe barrel 46, such that the conical lip 21 drives the needle 4 to move forwards to enable the conical hole 22 of the needle 4 to be separated from the conical fitting 50 of the syringe barrel 46.

The thumbpress 54 of the plunger rod 47 has a notch 65 on the side of the catcher 58 (refer to FIG. 22 and FIG. 23). Before the medical syringe 45 is used, the needle 4 is put into the catcher 58 of the plunger rod 47 (refer to FIG. 22), When the medical syringe 45 is used, the conical lip 21 of the needle 4 which is put into the catcher 58 of the plunger rod 47 is nipped at the notch 65 of the thumbpress 54 of the plunger rod 47, then the needle 4 is taken out of the side opening of the catcher 58, and then the conical hole 22 of the needle 4 is plugged onto the conical fitting 50 of the syringe barrel 46 such that the needle 4 is fixed onto the conical fitting 50 of the syringe barrel 46 (refer to FIG. 23).

An inward locking circumferential wedge 66 is provided at a rear part of the chamber 48 (refer to FIG. 25 to FIG. 27 and FIG. 30). A large-inclination-angle wedge's axial constraint inclined surface 67 is provided in an axial direction of the locking circumferential wedge 66. Large-inclination-angle wedge's circumferential constraint inclined surfaces 68 and 69 are provided on both sides of a circumferential direction of the locking circumferential wedge 66 respectively. A locking circumferential groove 70 is provided at a periphery of the plunger rod 47 (refer to FIG. 25 to FIG. 27 and FIG. 29). A large-inclination-angle groove's axial constraint inclined surface 71 is provided in an axial direction of the locking circumferential groove 70. Large-inclination-angle groove's circumferential constraint inclined surfaces 72 and 73 are provided on both sides of a circumferential direction of the locking circumferential groove 70 respectively. A locking axial wedge 74 is provided on a side surface of the circumferential direction of the locking circumferential groove 70. When the medical syringe 45 is used, the locking axial wedge 74 of the plunger rod 47 prevents the locking circumferential wedge 66 in the chamber 48 from crossing the locking axial wedge 74 of the plunger rod 47 and entering the locking circumferential groove 70 of the plunger rod 47. After the medical syringe 45 is used and after the needle 4 plugged onto the conical fitting 50 of the syringe barrel 46 is taken down, the needle 4 is put into the catcher 58 of the plunger rod 47 (refer to FIG. 22). When the stopper 55 of the plunger rod 47 is located at the distal wall 49 of the syringe barrel 46, the plunger rod 47 is rotated such that the locking circumferential wedge 66 in the chamber 48 is elastically deformed to cross the locking axial wedge 74 of the plunger rod 47 and enter the locking circumferential groove 70 of the plunger rod 47, the large-inclination-angle groove's axial constraint inclined surface 71 of the locking circumferential groove 70 of the plunger rod 47 and the large-inclination-angle wedge's axial constraint inclined surface 67 of the locking circumferential wedge 66 in the syringe barrel 48 constrain each other to prevent the plunger rod 47 from moving forwards and backwards in the chamber 48, and the two large-inclination-angle groove's circumferential constraint inclined surfaces 72 and 73 of the locking circumferential groove 70 of the plunger rod 47 and the two large-inclination-angle wedge's circumferential constraint inclined surfaces 68 and 69 of the locking circumferential wedge 66 in the chamber 48 respectively constrain each other to prevent the plunger rod 47 from rotating in the chamber 48 (refer to FIG. 25 to FIG. 27); and at the same time, an audible sound made when the locking circumferential wedge 66 in the chamber 48 is elastically deformed prompts that the plunger rod 47 and the needle 4 which is put into the catcher 58 of the plunger rod 47 have already been locked in the syringe barrel 46.

A circumferential protection wedge 75 is provided at a proximal end of the locking circumferential groove 70 of the plunger rod 47 (refer to FIG. 29). After the plunger rod 47 is rotated such that the locking circumferential wedge 66 in the chamber 48 is elastically deformed to cross the locking axial wedge 74 of the plunger rod 47 and enter the locking circumferential groove 70 of the plunger rod 47, the circumferential protection wedge 75 covers a proximal end of the locking circumferential wedge 66 in the chamber 48 (refer to FIG. 26) to prevent the locking circumferential wedge 66 in the chamber 48 which has already entered the locking circumferential groove 70 of the plunger rod 47 from being artificially pulled off the locking circumferential groove 70 of the plunger rod 47.

Figure 31:
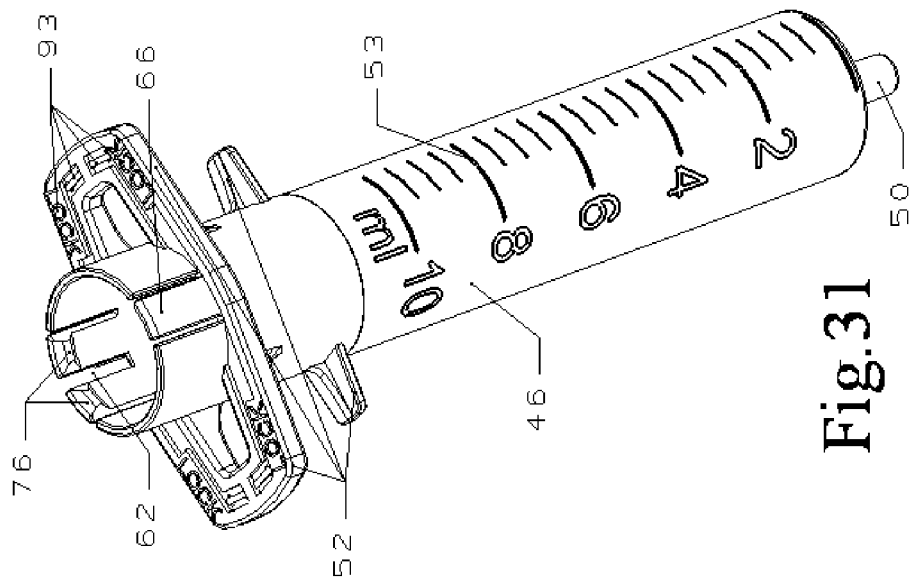
FIG. 31 is a perspective view of a hack side of FIG. 30.
Figure 30:
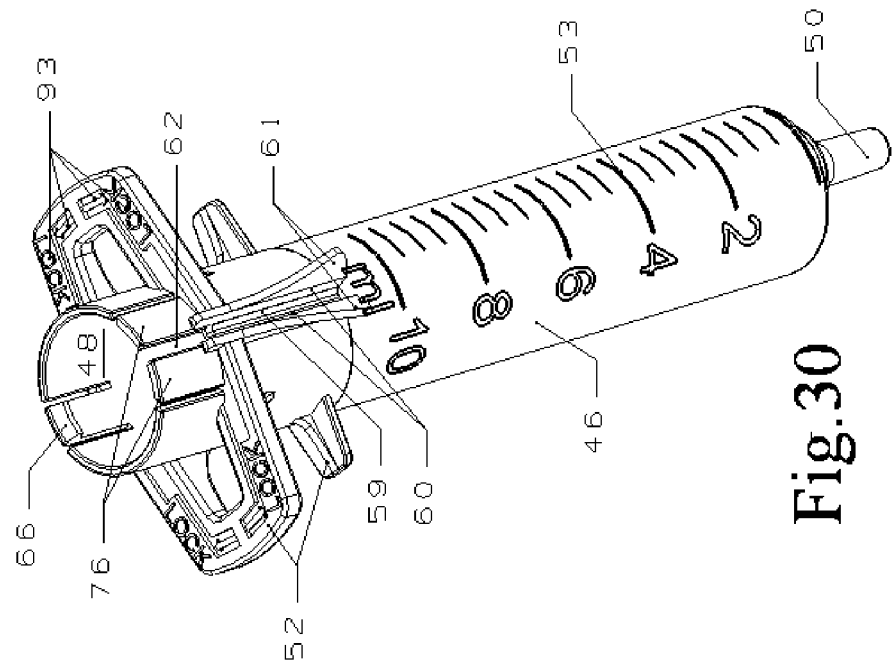
FIG. 30 is a perspective view of a syringe barrel of the medical syringe in FIG. 21.

A locking mark 93 is provided on a rear side surface of the peripheral flange 52 of the syringe barrel 46 (refer to FIG. 30 and FIG. 31). After the plunger rod 47 is rotated according to a direction indicated by the locking mark 93, the plunger rod 47 is capable of being locked on the syringe barrel 46.

An inward positioning circumferential wedge 76 is provided at a rear part of the chamber 48 (refer to FIG. 16 to FIG. 21 and FIG. 31). Wedge's axial constraint inclined surfaces 77 and 78 are provided on both sides of an axial direction of the positioning circumferential wedge 76 respectively. Wedge's circumferential constraint inclined surfaces 79 and 80 are provided on both sides of a circumferential direction of the positioning circumferential wedge 76 respectively. The plurality of positioning circumferential grooves 81 are provided at a periphery of the plunger rod 47 (refer to FIG. 16 to FIG. 21). The plurality of positioning circumferential grooves 81 are arranged and distributed along an axial direction of the plunger rod 47. Groove's axial constraint inclined surfaces 82 and 83 are provided on both sides of an axial direction of each positioning circumferential groove 81 respectively. Groove's circumferential constraint inclined surfaces 84 and 85 are provided on both sides of a circumferential direction of each positioning circumferential groove 81 respectively. A positioning axial wedge 86 is provided on a side surface of a circumferential direction of the positioning circumferential groove 81. A wedge's circumferential constraint inclined surface 87 is provided on a side surface of a circumferential direction of the positioning axial wedge 86. After the plunger rod 47 is rotated such that the positioning circumferential wedge 76 in the chamber 48 is elastically deformed to cross the wedge's circumferential constraint inclined surface 87 of the positioning axial wedge 86 of the plunger rod 47 and enter a selected positioning circumferential groove 88 of the plunger rod 47, two groove's circumferential constraint inclined surfaces 89 and 90 of the selected positioning circumferential groove 88 of the plunger rod 47 and the two wedge's circumferential constraint inclined surfaces 79 and 80 of the positioning circumferential wedge 76 in the chamber 48 constrain each other to prevent the plunger rod 47 from rotating in the chamber 48, and two groove's axial constraint inclined surfaces 91 and 92 of the selected positioning circumferential groove 88 of the plunger rod 47 and the two wedge's axial constraint inclined surfaces 77 and 78 of the positioning circumferential wedge 76 in the chamber 48 constrain each other to prevent the stopper 55 of the plunger rod 47 from moving forwards and backwards in the chamber 48, thus, a chamber between a front end of the stopper 55 of the plunger rod 47 constrained in the chamber 48 and the distal wall 49 of the chamber 48 forms a selected liquid filling volume of the medical syringe 45 (refer to FIG. 16 and FIG. 21). After the plunger rod 47 is rotated such that the positioning circumferential wedge 76 in the chamber 48 is elastically deformed to cross the groove's circumferential constraint inclined surface 89 of the selected positioning circumferential groove 88 of the plunger rod 47 and be removed out of the selected positioning circumferential groove 88 of the plunger rod 47, the wedge's circumferential constraint inclined surface 87 of the positioning axial wedge 86 of the plunger rod 47 prevents the positioning circumferential wedge 76 in the chamber 48 from entering the positioning circumferential groove 81 of the plunger rod 47, and the stopper 55 is capable of moving forwards and backwards in the chamber 48 by manipulating the thumbpress 54 of the plunger rod 47 (refer to FIG. 22 and FIG. 23). In an operation process, an audible sound made when the positioning circumferential wedge 76 in the chamber 48 is elastically deformed prompts that the working state of the medical syringe 45 has already been changed.

Figure 32:
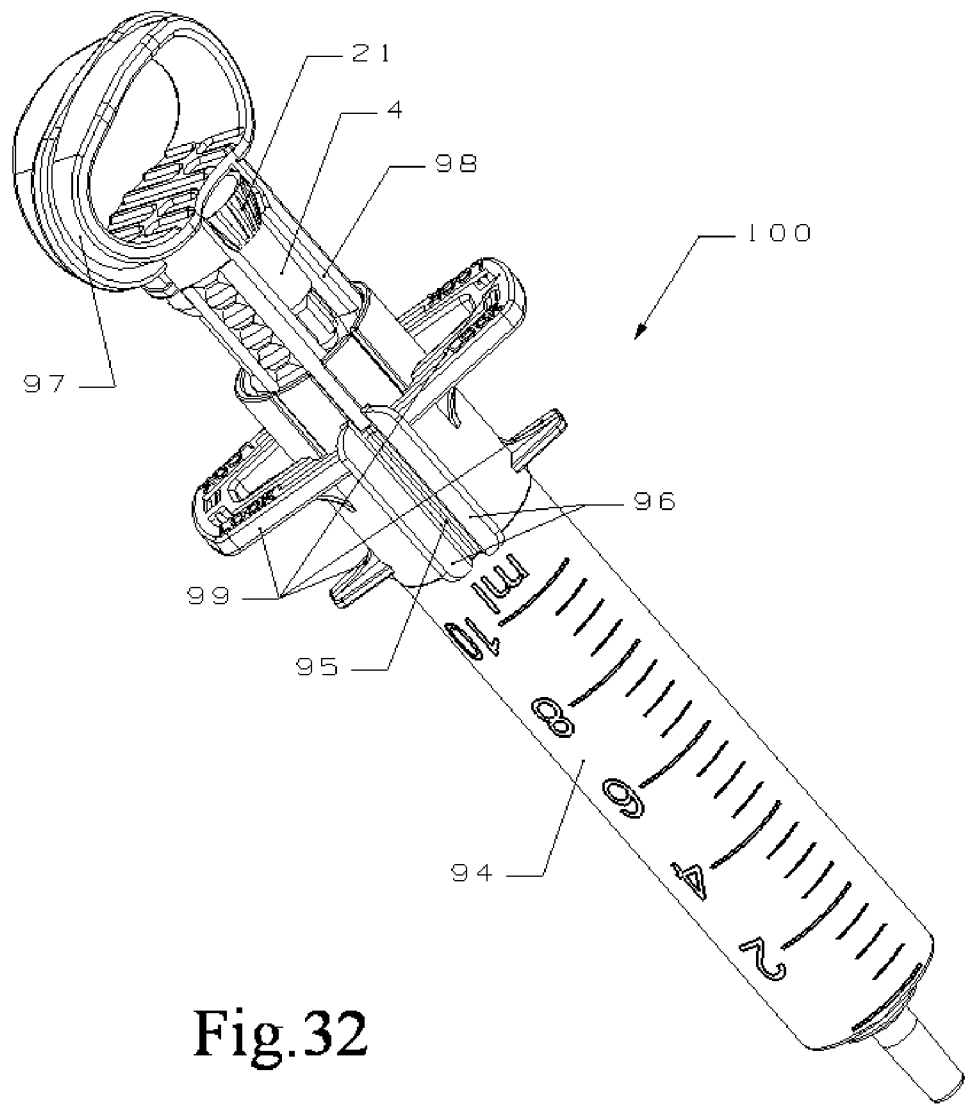
FIG. 32 is a perspective view of another medical syringe similar to the medical syringe in FIG. 21.

The syringe barrel 46 of the medical syringe 45 may also be replaced with a syringe barrel 94. The height of a front part of a wing 96 obliquely extending on both sides of a needle guide groove 95 of the syringe barrel 94 is the same as the height of a rear part (refer to FIG. 32). The plunger rod 47 of the medical syringe 45 may also be replaced with a plunger rod 98 with an annular thumbpress 97 (refer to FIG. 32). The annular thumbpress 97 of the plunger rod 98 cooperates with a peripheral flange 99 of the syringe barrel 94 such that the medical syringe 100 can be more conveniently operated by a single hand.

According to the above-mentioned detailed description, it can be seen that the medical syringe provided by the present invention can achieve the following technical effects:

The medical syringe provided by the present invention realizes that a conical fitting and a conical inclined surface of a syringe barrel and a conical lip and a conical hole of a needle form an interface of the needle. When the conical hole of the needle is plugged onto the conical fitting of the syringe barrel, the needle is fixed onto the conical fitting of the syringe barrel to achieve the purpose of preventing a needle tip of the needle from swinging when the needle pierces a muscle or a blood vessel of a human body, so as to avoid misoperation. After the medical syringe is used, the conical lip of the needle distal away from the needle tip only needs to be pinched flat, the needle can then be separated from the conical fitting of the syringe barrel of the medical syringe, and thus not only the contaminated needle can be put into a collection box, but also the contaminated needle can be collected into an catcher of a plunger rod of the medical syringe. The purpose of preventing contact with the needle tip in an operation process is achieved and thus the contaminated needle is prevented from injuring the human body.

The medical syringe provided by the present invention realizes that one side of a plunger rod has a catcher with a side opening in which a needle can be put, and a thumbpress of the plunger rod has a notch in one side of the catcher. Before the medical syringe is used, the needle is put into the catcher of the plunger rod. When the medical syringe is used, the conical lip of the needle which is put into the catcher of the plunger rod is nipped at the notch of the thumbpress of the plunger rod, and the needle is taken out of the side opening of the catcher. After the medical syringe is used, and after the needle plugged onto the conical fitting of the syringe barrel is taken down, then the needle is put into the catcher of the plunger rod from the side opening of the catcher, and then the plunger rod is pushed to the end such that most part of the plunger rod enters the syringe barrel, so as to achieve the purpose that the overall volume of the finally formed medical syringe is smaller, thereby facilitating the subsequent destruction treatment.

The medical syringe provided by the present invention realizes that a plunger rod has a catcher with a side opening in which a needle can be put; at a rear part of an outer wall of the syringe barrel, an axial needle guide groove is provided on the same side of the catcher of the plunger rod, and a wing obliquely extending towards both sides of the needle guide groove is respectively provided on an outer side of the rib on both sides of the needle guide groove, After the needle plugged onto the conical fitting of the syringe barrel is taken down, a needle tip is moved backwards along the needle guide groove, the wings on the both sides of the needle guide groove facilitate introducing the needle tip into the needle guide groove, and the ribs on the both sides of the needle guide groove prevents the needle tip from sliding out of the needle guide groove when moving backwards along the needle guide groove till the needle enters the catcher of the plunger rod from the side opening of the catcher of the plunger rod. The purpose of preventing contact with the needle tip in an operation process is achieved, and thus the contaminated needle is prevented from seriously injuring the human body.

The medical syringe provided by the present invention realizes that an inward locking circumferential wedge is provided at a rear part of a chamber, a locking circumferential groove is provided at a periphery of a plunger rod, a circumferential protection wedge is provided at a proximal end of the locking circumferential groove of the plunger rod, and the locking circumferential wedge in the chamber is capable of being elastically deformed to cross the locking circumferential wedge of the plunger rod and enter the locking circumferential groove of the plunger rod; realizes that a locking mark is provided on a rear side surface of the peripheral flange of the syringe barrel; realizes that the plunger rod has a catcher with a side opening in which the needle can be put, and the thumbpress of the plunger rod has a notch in the side of the catcher; and realizes that a conical fitting and a conical inclined surface of the syringe barrel and a conical lip and a conical hole of the needle form an interface of the needle. After the medical syringe is used, the conical lip of the needle distal away from the head of the needle is pinched flat, the needle can be separated from the conical fitting of the syringe barrel of the medical syringe, and not only can the contaminated needle be put into a collection box, but also the contaminated needle can enter the catcher of the plunger rod from the side opening of the catcher of the plunger rod, then the plunger rod is pushed to the end, and then the plunger rod is rotated according a direction indicated by the locking mark such that the locking circumferential wedge in the chamber is elastically deformed to cross the locking axial wedge of the plunger rod and enter the locking circumferential groove of the plunger rod, and the plunger rod and the needle in the catcher of the plunger rod is thus locked in the chamber, and at this moment, the circumferential protection wedge covers the proximal end of the locking circumferential wedge in the chamber to prevent the locking circumferential wedge of the chamber which has already entered the locking circumferential groove of the plunger rod from being artificially pulled off the locking circumferential groove of the plunger rod, it not only achieves the purpose of preventing contact with the needle tip in the operation process, but also achieves that the overall volume of the finally formed medical syringe is smaller, and thus not only the contaminated needle can be prevented from seriously injuring the human body, but also reuse can be avoided and convenience can be brought to the subsequent destruction treatment.

The medical syringe provided by the present invention realizes that an inward positioning circumferential wedge is provided at a rear part of a chamber, and a positioning axial wedge and a plurality of positioning circumferential grooves arranged and distributed along an axial direction of the plunger rod are provided at a periphery of a plunger rod, After the plunger rod is rotated such that the positioning circumferential wedge in the chamber is elastically deformed to cross the positioning axial wedges of the plunger rod and enter a selected positioning circumferential groove of the plunger rod, a chamber between the stopper of the plunger rod constrained in the chamber and the distal wall of the chamber forms a selected liquid filling volume of the medical syringe; and after the plunger rod is rotated such that the positioning circumferential wedge in the chamber is elastically deformed to cross the positioning circumferential groove of the plunger rod and be removed out of the positioning circumferential groove of the plunger rod, the stopper is capable of moving forwards and backwards in the chamber by manipulating the thumbpress of the plunger rod. The purpose that the liquid filling amount of the medical syringe can be accurately locked is achieved.

The medical syringe provided by the present invention realizes that the parts of the sterile safety syringe for single use provided by the present invention have one less part, i.e., a sheath of a needle, than the conventional sterile syringe for single use; and realizes that the structure of the liquid filing chamber of the sterile safety syringe for single use provided by the present invention is the same as the structure of the conventional sterile syringe for single use. The safety-type disposable aseptic syringe provided by the present invention not only achieves the purposes of facilitating exhausting gas in the liquid filling chamber and facilitating assembly, but also achieves the purpose that the production cost is almost the same as the production cost of the conventional sterile syringe for single use and is much lower than the production cost of the existing sterile safety syringe for single use.

Therefore, it can be seen that the objectives, including the objectives shown by the above descriptions, are effectively achieved. Only typical and preferred embodiments of the present invention are described herein, and some changes may be made to the aforementioned structures without departing from the spirit and scope of the present invention. The present invention is not limited to or confined by the described specific details, and shall include, as stated in the claims, any improvement or modification obvious to persons of ordinary skill in the art.

What is claimed is:

1. An interface of a needle of a medical syringe, the medical syringe comprises a syringe barrel and a plunger rod;

the syringe barrel has a chamber which is respectively provided with an opening at a front end and a proximal end, a distal wall is provided at the front end of the chamber, a conical fitting is provided at a front end of the distal wall of the chamber, a passageway is provided inside the conical fitting and communicated with the chamber, a peripheral flange is provided at a rear part of the syringe barrel, and a volume scale is provided at an outer surface of the syringe barrel;

a thumbpress is provided at a proximal end of the plunger rod and a stopper is provided at a front part; said stopper is capable of moving forwards and backwards in the chamber by manipulating the thumbpress of the plunger rod, and an outer wall of the stopper and an inner wall of the chamber form a sealing fit of the medical syringe after the stopper of the plunger rod is plugged into the chamber from the opening in the proximal end of the chamber;

wherein said needle is capable of being plugged onto said conical fitting of the syringe barrel, a conical inclined surface is provided at a proximal end of said conical fitting of the syringe barrel, wherein said needle has a conical lip and a conical hole at a rear part, wherein said conical lip of the needle is located at a rear part of said conical hole, wherein the conical fitting and said conical inclined surface of the syringe barrel and the conical lip and the conical hole of the needle form an interface of the needle; wherein the needle is fixed onto the conical fitting of the syringe barrel when the conical hole of the needle is plugged onto the conical fitting of the syringe barrel; wherein the conical lip moves along the conical inclined surface of the proximal end of the conical fitting of the syringe barrel, such that the conical lip drives the needle to move forwards to enable the conical hole of the needle to be separated from the conical fitting of the syringe barrel when the conical lip of the needle is pinched flat.

2. The interface of the needle of the medical syringe according to claim 1, wherein axial grooves are distributed in a wall of the conical lip of the needle.

3. The interface of the needle of the medical syringe according to claim 1, wherein a catcher with a side opening is provided on one side of said plunger rod, wherein said needle can be put in said catcher, wherein an in-cavity circumferential groove is provided at a proximal end of the catcher, wherein the circumferential width of the side opening of said in-cavity circumferential groove of the catcher is smaller than the diameter of said conical lip of the needle and the diameter of the in-cavity circumferential groove of the catcher; wherein the conical lip of the needle is elastically deformed to cross the side opening of the in-cavity circumferential groove of the catcher and enter the in-cavity circumferential groove of the catcher, such that the conical lip of the needle is constrained in the in-cavity circumferential groove of the catcher and the needle is constrained in the catcher when the needle is put into the catcher of the plunger rod.

4. The interface of the needle of the medical syringe according to claim 3, wherein said thumbpress of the plunger rod has a notch on the side of said catcher; wherein said needle is put into the catcher of the plunger rod before said medical syringe is used; wherein said conical lip of the needle put into the catcher of the plunger rod is nipped at said notch of the thumbpress of the plunger rod, then the needle is taken out of said side opening of the catcher, and then said conical hole of the needle is plugged onto said conical fitting of the syringe barrel such that the needle is fixed onto the conical fitting of the syringe barrel when the medical syringe is used.

5. The interface of the needle of the medical syringe according to claim 4, wherein said needle is put into said catcher of said plunger rod from the side opening of the catcher after said medial syringe is used, and after the needle plugged onto said conical fitting of the syringe barrel is taken down.

6. The interface of the needle of the medical syringe according to claim 3, wherein at a rear part of an outer wall of said syringe barrel, an axial needle guide groove is provided on the same side of said catcher of the plunger rod, wherein an axial rib is provided on both sides of said needle guide groove respectively, wherein a wing obliquely extending towards both sides of the needle guide groove is respectively provided on an outer side of said rib, wherein the ribs on the both sides of the needle guide groove and the outer wall of said syringe barrel form the needle guide groove; wherein a needle tip is moved backwards along the needle guide groove, and said wing on the both sides of the needle guide groove facilitates introducing the needle tip into the needle guide groove, and the ribs on the both sides of the needle guide groove prevent the needle tip from sliding out of the needle guide groove till said needle enters the catcher of the plunger rod from the side opening of the catcher of the plunger rod when moving backwards along the needle guide groove after the needle plugged onto said conical fitting of the syringe barrel is taken down.

7. The interface of the needle of the medical syringe according to claim 6, wherein said syringe barrel has a side opening corresponding to the position of said catcher of the plunger rod in a rear part of said needle guide groove; wherein said needle tip is moved backwards to said side opening of the syringe barrel along the needle guide groove such that the needle enters said catcher of the plunger rod from said side opening of the catcher of the plunger rod after said needle plugged onto said conical fitting of the syringe barrel is taken down.

8. The interface of the needle of the medical syringe according to claim 1, wherein an inward locking circumferential wedge is provided at a rear part of said chamber, wherein a wedge's axial constraint inclined surface is provided in an axial direction of said locking circumferential wedge, wherein a wedge's circumferential constraint inclined surface is respectively provided on both sides of a circumferential direction of the locking circumferential wedge; wherein a locking circumferential groove is provided at a periphery of said plunger rod, wherein a groove's axial constraint inclined surface is provided in an axial direction of said locking circumferential groove, wherein a groove's circumferential constraint inclined surface is respectively provided on both sides of a circumferential direction of the locking circumferential groove, wherein a locking axial wedge is provided on a side surface of the circumferential direction of the locking circumferential groove; wherein said groove's axial constraint inclined surface of the locking circumferential groove of the plunger rod and the wedge's axial constraint inclined surface of the locking circumferential wedge in the syringe barrel constrain each other, and two groove's circumferential constraint inclined surfaces of the locking circumferential groove of the plunger rod and two wedge's circumferential constraint inclined surfaces of the locking circumferential wedge in the chamber respectively constrain each other, such that the plunger rod is locked on the chamber after the plunger rod is rotated such that the locking circumferential wedge in the chamber is elastically deformed to cross the locking axial wedge of the plunger rod and enter the locking circumferential groove of the plunger rod.

9. The interface of the needle of the medical syringe according to claim 8, wherein a block is provided at a front end between said two locking axial wedges of the plunger rod; wherein said wedge's axial constraint inclined surface of the locking circumferential wedge of the chamber prevents said block of the plunger rod from further moving backwards to prevent the plunger rod from being separated from said syringe barrel from said opening at the proximal end of the chamber when the plunger rod moves backwards to the opening in the proximal end of the chamber.

10. The interface of the needle of the medical syringe according to claim 8, wherein a circumferential protection wedge is provided at a proximal end of said locking circumferential groove of the plunger rod; wherein said circumferential protection wedge covers a proximal end of said locking circumferential wedge in the chamber after the locking circumferential wedge in the chamber enters the locking circumferential groove of the plunger rod.

11. The interface of the needle of the medical syringe according to claim 8, wherein a locking mark is provided on a rear side surface of said peripheral flange of the syringe barrel; wherein said plunger rod is capable of being locked on the syringe barrel after the plunger rod is rotated according to a direction indicated by said locking mark.

12. The interface of the needle of the medical syringe according to claim 1, wherein an inward positioning circumferential wedge is provided at a rear part of said chamber, wherein wedge's axial constraint inclined surfaces are respectively provided on both sides of an axial direction of said positioning circumferential wedge, and wherein wedge's circumferential constraint inclined surfaces are respectively provided on both sides of a circumferential direction of the positioning circumferential wedge; wherein a plurality of positioning circumferential grooves are provided at a periphery of said plunger rod, wherein said plurality of positioning circumferential grooves are arranged and distributed along an axial direction of the plunger rod, wherein groove's axial constraint inclined surfaces are respectively provided on both sides of an axial direction of each positioning circumferential groove, wherein groove's circumferential constraint inclined surfaces are respectively provided on both sides of a circumferential direction of each positioning circumferential groove, wherein a positioning axial wedge is provided on a side surface of a circumferential direction of the positioning circumferential groove, and wherein a wedge circumferential constraint inclined surface is provided on a side surface of a circumferential direction of the positioning axial wedge; wherein two said groove's circumferential constraint inclined surfaces of the selected positioning circumferential groove of the plunger rod and two said wedge's circumferential constraint inclined surfaces of the positioning circumferential wedge in the chamber constrain each other to prevent the plunger rod from rotating in the chamber, wherein two said groove's axial constraint inclined surfaces of the selected positioning circumferential groove of the plunger rod and two said wedge's axial constraint inclined surfaces of the positioning circumferential wedge in the chamber constrain each other to prevent the stopper of the plunger rod from moving forwards and backwards in the chamber such that a chamber between a front end of the stopper of the plunger rod constrained in the chamber and the distal wall of the chamber forms a selected liquid filling volume of the medical syringe after the plunger rod is rotated such that the positioning circumferential wedge in the chamber is elastically deformed to cross the wedge's circumferential constraint inclined surface of the positioning axial wedge of the plunger rod and enter a selected positioning circumferential groove of the plunger rod; and wherein the wedge's circumferential constraint inclined surface of the positioning axial wedge of the plunger rod prevents the positioning circumferential wedge in the chamber from entering the positioning circumferential groove of the plunger rod, wherein the stopper is capable of moving forwards and backwards in the chamber by manipulating the thumbpress of the plunger rod after the plunger rod is rotated such that the positioning circumferential wedge in the chamber is elastically deformed to cross the groove's circumferential constraint inclined surface of the positioning circumferential groove of the plunger rod and be removed out of the positioning circumferential groove of the plunger rod.

* * * * *